(12) United States Patent
Reid et al.

(10) Patent No.: US 8,404,483 B2
(45) Date of Patent: Mar. 26, 2013

(54) PARACRINE SIGNALS FROM MESENCHYMAL FEEDER CELLS AND REGULATING EXPANSION AND DIFFERENTIATION OF HEPATIC PROGENITORS USING SAME

(75) Inventors: Lola M. Reid, Chapel Hill, NC (US); Randall E. McClelland, Chapel Hill, NC (US); Joshua Uronis, Durham, NC (US); Hsin-Lei Yao, Chapel Hill, NC (US); Eliane Wauthier, Chapel Hill, NC (US)

(73) Assignee: University of North Carolina at Chapel Hill, Chapel Hill, NC (US)

(*) Notice: Subject to any disclaimer, the term of this patent is extended or adjusted under 35 U.S.C. 154(b) by 0 days.

(21) Appl. No.: 12/923,253

(22) Filed: Sep. 10, 2010

(65) Prior Publication Data

US 2011/0065188 A1 Mar. 17, 2011

Related U.S. Application Data

(63) Continuation of application No. 12/213,100, filed on Jun. 13, 2008, now abandoned.

(60) Provisional application No. 60/944,435, filed on Jun. 15, 2007.

(51) Int. Cl.
*C12N 5/00* (2006.01)
*C12N 5/02* (2006.01)

(52) U.S. Cl. .................. 435/373; 435/370; 435/366

(58) Field of Classification Search .............. 435/373, 435/370, 366
See application file for complete search history.

(56) References Cited

U.S. PATENT DOCUMENTS

| 5,576,207 A * | 11/1996 | Reid et al. ............ 435/378 |
|---|---|---|
| 6,069,005 A | 5/2000 | Reid et al. |
| 7,759,118 B2 * | 7/2010 | Reid et al. ............ 435/325 |
| 2002/0182188 A1 | 12/2002 | Reid et al. |
| 2003/0032182 A1 | 2/2003 | Kubota et al. |
| 2004/0018621 A1 | 1/2004 | Reid et al. |
| 2007/0099297 A1 | 5/2007 | Reid et al. |
| 2007/0134789 A1 | 6/2007 | Reid et al. |
| 2007/0155009 A1 | 7/2007 | McClelland et al. |
| 2008/0026463 A1 | 1/2008 | Ruiz et al. |
| 2008/0248570 A1 | 10/2008 | Turner et al. |

FOREIGN PATENT DOCUMENTS

| WO | WO-2007/059501 A2 | 5/2007 |
|---|---|---|
| WO | WO 2007/059501 A2 | 5/2007 |
| WO | WO 2008/109659 A2 | 9/2008 |

OTHER PUBLICATIONS

Zhang et al. Hepatology, 48(5): 1598-1607,2008.
Schmeizer et al. J. of Exp. Med., 204(8): 1973-1987,2007.
Köhler et al. Stem Cells, 17: 19-24, 1999.
Amit et al. Biol. of Reprod., 70: 837-845, 2004.
U.S. Appl. No. 09/678,953, filed Oct. 3, 2000, Kubota.
U.S. Appl. No. 09/679,663, filed Oct. 3, 2000, Kubota.
Agelli et al. Putative Liver Progenitor Cells: Conditions for Long-Term Survival in Culture. Histochemical Journal, 1997, vol. 29, pp. 205-217.
Brill S. et al. "Hepatic Progenitor Populations in Embryonic, Neonatal, and Adult Liver" Proceedings of the Society for Experimental Biology & Medicine, Academic Press, Inc., NY US, vol. 204, No. 3, Dec. 1993, pp. 261-269.
Chen, Q. et al., "Selective Proliferation of Rat Hepatocyte Progenitor Cells in Serum-free Culture," Nature Protocols, vol. 2, No. 5, May 2007, pp. 1197-1205.
Qin, Al et al., "Effects of Growth Factors and Extracellular Matrix on Proliferation and Differentiation of Fetal Liver Progenitor Cell in Vitro," Database Medline [Online] US National Library of Medicine, Jul. 2004, Database Accession No. NLM15268804.
Search Report and Written Opinion mailed Sep. 10, 2008 in Intl Appln No. PCT/US2008/07397.
Sugimoto, S. et al., "Morphological Changes Induced by Extracellular Matrix are Correlated with Maturation of Rat Small Hepatocytes," Journal of Cellular Biochemistry, vol. 87, No. 1, 2002, pp. 16-28.
Supplementary Search Report mailed Jul. 6, 2010 in European Appln No. 08768437.9.
Turner, W. et al., "Human Hepatoblast Phenotype Maintained by Hyaluronan Hydrogels" Journal of Biomedical Materials Research. Part B: Applied Biomaterials, 2007, vol. 82B, pp. 156-168.
Written Opinion mailed Feb. 15, 2011 in Singapore Appln No. 200908328-8.
Agelli et al. "Putative Liver Progenitor Cells: Conditions for Long-Term Survival in Culuture", Histochemical Journal, vol. 29, No. 3, 1997, pp. 205-217, XP008092875.
Turner et al. "Human Hepatoblast Phenotype Maintained by Hyaluronan Hydrogels", Journal of Biomedical Materials Research, vol. 82B, No. 1, Dec. 20, 2006, pp. 156-168, XP009104432.

* cited by examiner

*Primary Examiner* — Thaian N Ton
(74) *Attorney, Agent, or Firm* — Gilberto M. Villacorta; Sunit Talapatra; Foley & Lardner LLP

(57) ABSTRACT

A method is provided for controlling the survival, proliferation, and/or differentiation of hepatic progenitors in vitro by using specific types of mesenchymal feeder cells or one of more of the paracrine signals produced by those feeders.

12 Claims, 15 Drawing Sheets
(9 of 15 Drawing Sheet(s) Filed in Color)

US 8,404,483 B2

PARACRINE SIGNALS FROM MESENCHYMAL FEEDER CELLS AND REGULATING EXPANSION AND DIFFERENTIATION OF HEPATIC PROGENITORS USING SAME

CROSS-REFERENCE TO RELATED PATENT APPLICATIONS

This application is a Continuation of U.S. patent application Ser. No. 12/213,100, filed Jun. 13, 2008, which claims priority from U.S. Provisional Application No. 60/944,435, filed Jun. 15, 2007, each of the above-identified applications is incorporated herein by reference in its entirety.

FIELD OF THE INVENTION

The present invention relates generally to the ex vivo propagation and/or differentiation of hepatic progenitor cells. More particularly, the present invention relates to the identification and selection of soluble and insoluble paracrine signals derived from mesenchymal cells and their application in regulating expansion and/or differentiation of hepatic progenitor cells, including hepatic stem cells, in vitro.

BACKGROUND OF THE INVENTION

Hepatic stem cells and their progeny (e.g., hepatoblasts and committed progenitors) have considerable expansion potential. For this reason, these cell populations are desirable candidates for cell therapies, including bioartificial livers or cell transplantation. Despite this promise, however, the full potential of liver cell therapy remains to be realized.

The in vitro propagation of hepatic stem cells and their progeny has proven to be challenging, in part, because in vitro culture conditions are not always optimal for transition from the laboratory bench to the clinic. For example, some culture conditions are not good for survival, can greatly retard cell division, or can promote cell differentiation towards undesired fates. As well, some culture conditions require the addition of factors (e.g., serum) that can introduce contaminants and thereby limit their application in treating humans.

Maintenance of normal cells, especially progenitors, requires feeders of mesenchymal companion cells, known to provide paracrine signals critical for survival and function of the progenitors. There is a need to identify categories of mesenchymal cell feeders and then to use them as models to identify their paracrine signals, extracellular matrix components and soluble signals, that mediate expansion, lineage restriction towards specific fates, or differentiation of hepatic progenitors towards their adult fates of biliary epithelia and hepatocytes. Defining the signals enables one to use the signals on their own in the proper combinations and without the feeders to elicit the desired biological responses from the hepatic progenitors and that includes survival, expansion, lineage restriction towards a fate, and full differentiation to mature liver cells. Thus, there is a need for culture conditions that are defined so as to obviate the heretofore requirement of feeder cells.

SUMMARY OF THE INVENTION

In one embodiment of the present invention, a method of propagating hepatic stem cells in vitro without inducing their differentiation is provided comprising: culturing a population of isolated hepatic stem cells in serum-free culture media and on a layer of matrix components selected from the group consisting of hyaluronans, other unsulfated or poorly sulfated glycosaminoglycans (GAGs), unsulfated or poorly sulfated proteoglycans, embryonic collagens (e.g., type III) and embryonic basal adhesion molecules, and combinations thereof, in which the layer is essentially free of mature collagens (e.g., type I), and in which the culturing propagates the hepatic stem cells without inducing their differentiation.

Any or all of the matrix components may be supplied by angioblast feeder cells, quiescent hepatic stellate feeder cells, HUVEC feeder cells, or a combination thereof. The basal adhesion molecules may comprise isoforms of laminin found predominantly in fetal tissues and the GAGs, other than hyaluronans, may be forms of chondroitin sulfates. The hepatic stem cells may be human and obtained from fetal, neonatal, pediatric or adult liver. The laminin may be supplied at a concentration between about 0.1 to about 2 $\mu g/cm^2$, preferably at a concentration of about 1 $\mu g/cm^2$. Similarly, the type III or IV collagens can be, individually, at a concentration between about 0.1 to about 15 $\mu g/cm^2$.

In another embodiment of the present invention, a method of differentiating hepatic stem cells in vitro to hepatoblasts is provided comprising: culturing a population of isolated hepatic stem cells in serum-free culture media and on a layer of matrix components selected from the group consisting of embryonic collagens, basal adhesion molecules, CS-PGs, and combinations thereof, in which the layer is essentially free of mature collagens, and in which the culturing propagates the hepatic stem cells without inducing their differentiation.

Any or all of the matrix components may be supplied by activated endothilia, activated hepatic stellate feeder cells, or both. The embryonic collagen can be a type IV collagen and the basal adhesion molecules may comprise fetal isoforms of laminin, supplied at a concentration between about 0.1 to about 2 $\mu g/cm^2$, preferably at a concentration of about 1 $\mu g/cm^2$. In some embodiments, the layer further comprises hyaluronans. The hepatic stem cells can be obtained from fetal, neonatal, pediatric or adult liver, and preferably from humans.

In yet another embodiment of the present invention, a method of differentiating hepatic stem cells or hepatoblasts in vitro into committed hepatocyte or biliary progenitors and progeny thereof is provided comprising: culturing a population of isolated hepatic stem cells in serum-free culture media and on a layer of matrix components selected from the group consisting of sulfated proteoglycans, mature collagens, fibronectin, and combinations thereof, and in which the culturing induces the differentiation of the hepatic stem cells or hepatoblasts into committed hepatic or biliary progenitors and progeny thereof. Any or all of the matrix components may be supplied by stromal feeder cells, activated hepatic stellate feeder cells, myofibroblast feeder cells, or combinations thereof. In some embodiments, the layer is substantially free of hyaluronans and the sulfated proteoglycans can be heparan sulfate-PG or heparin-PG, or both.

In still yet another embodiment of the present invention, a container for propagation of hepatic progenitors or differentiating them is provided. The containers comprise a layer of matrix components selected from the group consisting of hyaluronans, other unsulfated or poorly sulfated glycosaminoglycans (GAGs), unsulfated or poorly sulfated proteoglycans, embryonic collagens and embryonic basal adhesion molecules, and combinations thereof; wherein the layer is essentially free of mature collagens; and wherein the layer of matrix components substantially coats at least one surface of the container.

Alternatively, the layer may comprise matrix components selected from the group consisting of embryonic collagens, basal adhesion molecules, CS-PGs, and combinations thereof, wherein the layer is essentially free of mature collagens; and wherein the layer of matrix components substantially coats at least one surface of the container. Finally, the layer may comprise matrix components selected from the group consisting of sulfated proteoglycans, mature collagens, fibronectin, and combinations thereof, wherein the layer of matrix components substantially coats at least one surface of the container. The container may be a tissue culture plate, a bioreactor, a lab cell or a lab chip.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

The patent or application file contains multiple figures executed in color. Copies of this patent or patent application publication with color figures will be provided by the Office upon request and with payment of the necessary fee.

DETAILED DESCRIPTION OF THE INVENTION

Figure 1:
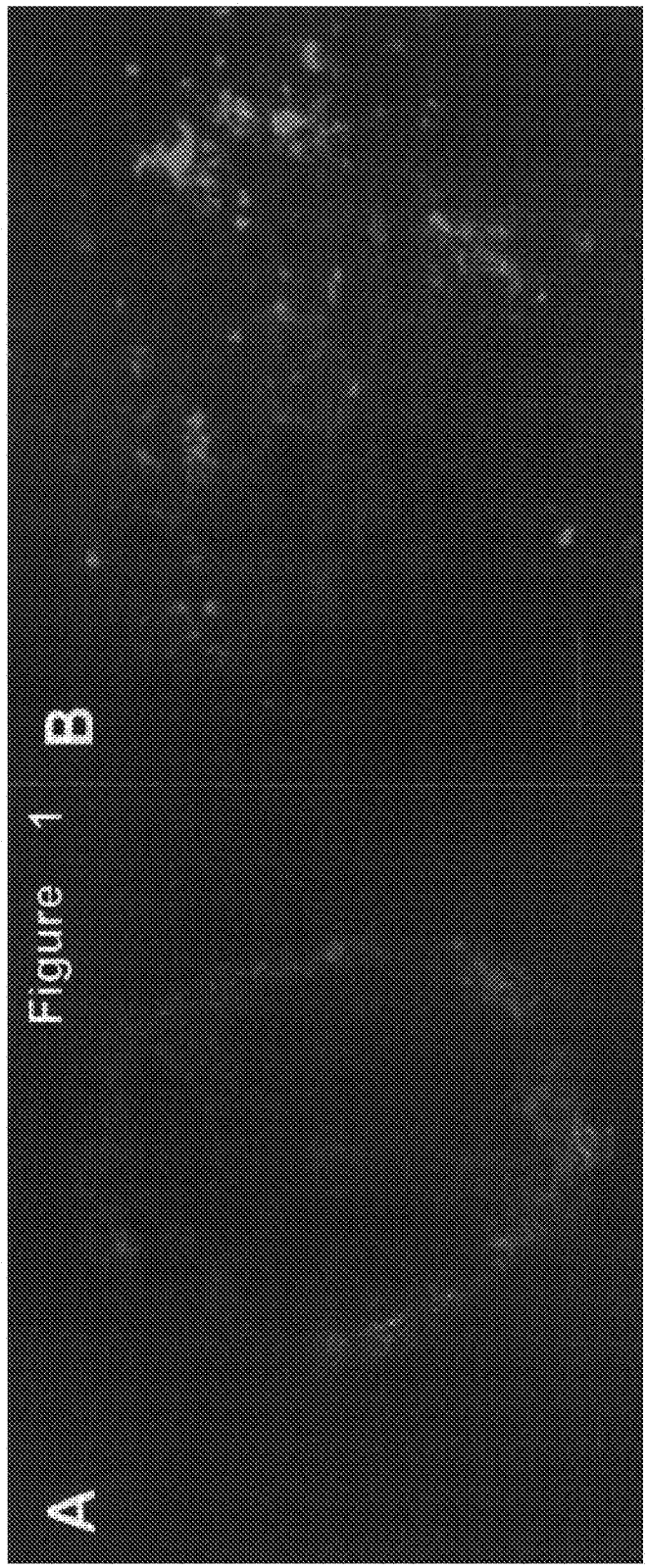
FIG. 1 shows a colony of hHpSCs and human hepatoblasts in culture: Both hHpSC colony (A) and human hepatoblasts (B) expressed EpCAM (shown in green). NCAM (shown in red, A) was expressed along the peripheral region and the center of the colony. Hepatoblasts strongly expressed alpha-fetoprotein (AFP, shown in red, B). Both cells were stained with DAPI (blue). Scale bar, 100 µm.

In one embodiment of the present invention, extracellular matrix components have been identified, which facilitate the attachment, survival and ex vivo proliferation and other matrix components that elicit the differentiation of hepatic stem cells and their progeny. The term "hepatic progenitors," as used herein, is broadly defined to encompass both hepatic stem cells and their progeny. "Progeny" may include both hepatic stem cells or hepatoblasts, both pluripotent progenitors thereof, and committed progenitors that can differentiate into only one lineage leading to particular mature cell type (e.g., a hepatocyte).

"Clonogenic expansion" refers to the growth property of cells that can expand from a single cell and be subcultured and expanded repeatedly with retention of the phenotype of the parental cell. "Colony formation" refers to the property of diploid parenchymal cells that can undergo a limited number of cell divisions (typically 5-7 cell divisions) within a week or two and involves cells with limited ability to undergo subculture or passaging. "Pluripotent" signifies cells that can form daughter cells of more than one fate; "unipotent" or "committed progenitors" are cells that have a single adult fate.

Hepatic stem cells (HpSCs) are pluripotent cells found in the ductal plates (also called limiting plates) in fetal and neonatal livers and in the Canals of Hering in pediatric and adult livers and showing evidence of self-replication with expression of telomerase and being capable of forming mature liver cells when transplanted. These cells are EpCAM+, NCAM+, ALB+, CK8/18+, CK19+, CD133/1+, and are negative for all hemopoietic markers tested (e.g., CD34, CD38, CD45, CD14), mesenchymal cell markers (CD146, VEGFr, CD31) and for expression of P450s or alpha-fetoprotein. The HpSCs have been found to give rise to hepatoblasts and to committed (unipotent) progenitors.

Hepatoblasts (HBs) are bipotent cells found throughout the parenchyma of fetal and neonatal livers and as single cells or small aggregates of cells tethered to the ends of the Canals of Hering. HBs derive from the HpSCs. HBs share many antigens present on HpSCs but with important distinctions. For example, HBs do not express NCAM but rather ICAM1 and they express significant amounts of alpha-fetoprotein and fetal forms of P450s. These HBs give rise to the unipotent progenitors, the committed hepatocytic and biliary progenitors.

Committed hepatic progenitors are unipotent progenitors of either the hepatocytic or biliary lineages. Their antigenic profile overlaps with that of the HBs; however, biliary committed progenitors express CK19 but not AFP or ALB, whereas the hepatocytic committed progenitors express AFP and ALB but not CK19. Committed biliary progenitors derive directly from hepatic stem cells and also from hepatoblasts.

Mesenchymal cells (MCs) include cells at various lineage stages of the many different mesenchymal cell types (listed as the mature cells and, in parentheses, their precursors): including stroma (mesenchymal stem cells), endothelia (angioblasts), stellate cells (stellate cell precursors), and various hemopoietic cells (hemopoietic stem cells)

While most, if not all, of the discussion and examples of hepatic progenitors herein will be with reference to human-derived cell populations, the teachings herein should not be limited to humans. In fact, one of ordinary skill in the art may be expected to apply the teachings herein to the expansion of hepatic progenitors from mammals, generally (e.g., mice, rats, dogs, etc.). Accordingly, the scope of the present invention is intended to include hepatic progenitors of any and all mammals.

It is also noted that hepatic progenitors suitable for in vitro propagation in accordance with the instant invention are not limited to those isolated or identified by any particular method. By way of example, methods for the isolation and identification of the hepatic progenitors have been described in, for example, U.S. Pat. No. 6,069,005 and U.S. patent application Ser. Nos. 09/487,318; 10/135,700; and 10/387,547, the disclosures of which are incorporated herein in their entirety by reference.

Hepatic stem cells and hepatoblasts have characteristic antigenic profiles and can be isolated by protocols described previously. For example, hepatic stem cells and hepatoblasts share numerous antigens (e.g., cytokeratins 8, 18, and 19, albumin, CD133/1, and epithelial cell adhesion molecule ("EpCAM")) and are negative for hemopoietic markers (e.g., glycophorin A, CD34, CD38, CD45, CD14) and mesenchymal cell markers (e.g., CD146, CD31, VEGFr or KDR). Alternatively, hepatic stem cells and hepatoblasts can be distinguished from each other by size (the stem cells are 7-9 μm; the hepatoblasts are 10-12 μm), by morphology in cultures (the stem cells form dense, morphologically uniform colonies, whereas the hepatoblasts form cord-like structures interspersed by clear channels, presumptive canaliculi), by distinctions in the pattern of expression of certain antigens (EpCAM is expressed throughout the hepatic stem cells but is confined to the cell surface in the hepatoblasts), or by distinct antigenic profiles (N-CAM is present in the hepatic stem cells, whereas alpha-fetoprotein (AFP) and ICAM1 are expressed by the hepatoblasts). In fetal and neonatal livers, the hepatic stem cells are in the ductal plates (also called "limiting plates"), whereas the hepatoblasts are the dominant parenchymal cell population (>80%). In pediatric and adult tissues, the hepatic stem cells are present in the Canals of Hering, whereas the hepatoblasts are cells tethered to the ends of the Canals of Hering. The hepatoblasts consist of small numbers of cells in normal tissue but found in large numbers (e.g., nodules) in diseased livers (e.g., cirrhosis).

The present invention provides methods to control ex vivo maintenance of HpSCs, preferably human HpSCs (hHpSCs), in vitro. More specifically, the inventive method enables propagation of HpSCs (1) without inducing differentiation (i.e., self-renewal); (2) inducing differentiation (i.e., "lineage restriction") of the HpSCs to hepatoblasts; or (3) inducing more "extensive" differentiation (e.g., into committed progenitors) (collectively referred herein a "ex vivo maintenance"). The method is enabled, in part, by the selective use of specific types of mesenchymal feeder cells used in co-cultures. The invention also provides insoluble (e.g., matrix molecules) and soluble (e.g., cytokines) components that alone or in combination allow for the propagation of HpSCs, if preferred, in the absence of feeder cells. Table 1 summarizes the insoluble factors discovered relevant to affect the aforementioned modes of ex vivo maintenance.

TABLE 1

Effects of Feeders/Substratum on Human Hepatic Stem/Progenitors

| | Substratum/Feeder | Morphology/antigenic profile of cells maintained on feeders for a week or more |
|---|---|---|
| | Plastic*** | hHpSC |
| | hUVECs | hHpSC |
| | hMSCs | Hepatoblasts |
| Liver Cell Suspensions immunoselected for: | KDR+ Cells in first week | hHpSCs |
| | KDR+ cells after 7-10 days | Initially mixture of hHpSCs and hepatoblasts that transitions rapidly to only hepatoblasts |
| | CD31+ Cells | Hepatoblasts |
| | Depleted of stromal cells | Hepatoblasts |

TABLE 1-continued

Effects of Feeders/Substratum on Human Hepatic Stem/Progenitors

| Substratum/Feeder | Morphology/antigenic profile of cells maintained on feeders for a week or more |
|---|---|
| STO cells | Growth-arrested hHpSCs differentiating to hepatoblasts and committed (unipotent) progenitors |
| Fibronectin | Few cells attached; those that did rapidly lost viability |
| Laminin | Hepatoblasts |
| Type III collagen | hHpSCs |
| Type IV collagen | Hepatoblasts |
| On surface of Type I collagen | Growth-arrested cells that are a mixture of hepatoblasts and committed (unipotent) progenitors |
| Embedded in Type I collagen | Mature hepatocytes |

All cultures were in serum-free KM.
***Note: when cells are on culture plastic, the hHpSC colonies survive only when they are in association with companion cells comprised of angioblasts and/or hepatic stellate cell precursors.
*Culture Morphology and antigenic profile:
hHpSC colonies are monolayers with cells of uniform morphology, high nucleus to cytoplasmic ratio, ~7-9 μm in diameter, tightly packed and surrounded by companion cells that include angioblasts and hHpSTCs. Unique Antigenic profile: NCAM+, Claudin 3+, albumin±, AFP−.
Hepatoblasts appear as colonies that are more 3-dimensional, with cord-like structure interspersed by clear channels (bile canaliculi) and with cells that are slightly larger (10-12 μm) in diameter. Unique antigenic profile: ICAM+, Claudin 3−, albumin ++, AFP++.
Shared antigenic profile between hHpSCs and hepatoblasts: positive for EpCAM, CK 8, 18, and 19, Indian Hedgehog proteins (sonic, Indian), telomerase; negative for hemopoietic markers (CD34, CD45, CD38, glycophorin A), for hepatic stellate cell markers (desmin and αSMA) and for endothelial cell markers (VEGFr, CD31, vWF).

Three distinct classes of feeders have been identified in keeping with the three modes of ex vivo maintenance outlined above. Co-culture with feeders of endothelia precursors or angioblasts free of human hepatic stellate cells (hHpSTCs) (or, in the alternative, comprising quiescent hHpSTCs) allow for the expansion of HpSCs without inducing their differentiation. Feeders replete with activated endothelia and hHpSTCs lineage restrict HpSCs to hepatoblasts. Finally, feeder cells comprising mature endothelia or murine stroma (represented by STO cells), lead HpSCs to differentiate into mature parenchymal cells (including, biliary and hepatocytic cells). It is presently believed that the behavior of the co-cultures thus identified parallels that observed during liver development, which is governed by paracrine signals from mesenchyme adjacent to the epithelium.

Matrix chemistry can be relevant to embryonic development. In one embodiment of the invention, the present inventors have found that extracellular matrix components found in or near the liver's stem cell niche, provide for expansion of hepatic progenitors without inducing differentiation better than existing technology. As described in U.S. patent application having Ser. No. 11/560,049 filed Nov. 15, 2006—the disclosure of which is incorporated herein in its entirety by reference—cells cultured on the matrix components, found in abundance in or near the liver's stem cell niche, aggregate to form spheroid-like structures on some of the matrix components (e.g., laminins) and spread into monolayers on others (e.g., type III collagen). Specific types of extracellular matrix components, found in the stem cell niche, are among the signals requisite for hepatic progenitor cells to undergo expansion in self-replication mode, that is symmetric cell divisions (the daughter cells are identical or nearly identical to the parent cells).

It is further believed that the maturation of hepatic stem cells occurs concomitantly with a unique combination of matrix components which direct, at least in part, their differentiation. Some extracellular matrix components are permissive for hepatic progenitors to undergo expansion associated with asymmetric divisions, that is expansion along with some differentiation. Yet others, located in regions of the liver tissue in which fully mature liver cells are found, elicit growth arrest and full differentiation of the cells.

All the feeders produce multiple categories of matrix components and that include basal adhesion molecules (fibronectin and/or laminin) and several collagens. Fibronectin proved to be a matrix component that was not expressed by the angioblasts or quiescent hHpSTCs but was expressed by all other feeders studied. It was produced at the highest levels by human umbilical vein endothelial cells (hUVECs) but the HpSCs do not attach well to it.

So, its presence in the matrices appears to be irrelevant to the biological responses induced by the feeders. The feeders that induced self-replication expressed type III and IV collagens, laminin and hyaluronans (angioblasts, quiescent HpSTCs, HUVEC cells). The feeders that induced lineage restriction to hepatoblasts and with continued expansion produced type IV collagen and laminin but not type III, some hyaluronans, and some chondroitin sulfate proteoglycan (primary cultures replete with activated HpSTCs, identified by elevated levels of αSMA and CD146). The feeders that induced the maximum differentiation expressed the highest amounts of matrix and that included high levels of type I and IV, laminin, fibronectin, and heparan sulfate proteoglycans.

Chondroitin sulfate proteoglycan (CS-PG) protein was evident in both human fibroblast-like, fetal liver-derived cells and bone marrow-derived mesenchymal stem cells (hMSCs). These two types of feeders caused lineage restriction of hHpSCs into hepatoblasts. Hence, CS-PGs likely signal, at least in part, that process. It has been hypothesized that the stem cell niche is dominated by glycosaminoglycans (GAGs) with little to no sulfation such as hyaluronans and these minimally sulphated CS-PGs could, therefore, act as a barrier minimizing the presentation of signals to the stem cells. As the stem cells are pushed out of the niche, they come into contact with GAGs and proteoglycans with more extensive sulfation and bind growth factors that could influence the stem cells either with respect to growth or with respect to lineage restriction to various differentiated cell fates.

The most extensive differentiation was observed in hHpSCs plated onto STO feeder cells, upon which the hHpSCs went into growth arrest and differentiated into hepatoblasts and unipotent progenitors (i.e., committed biliary and hepatocytic progenitors). The STO feeders produced the highest levels of extracellular matrix proteins and were unique in producing HS-PGs.

Figure 10:
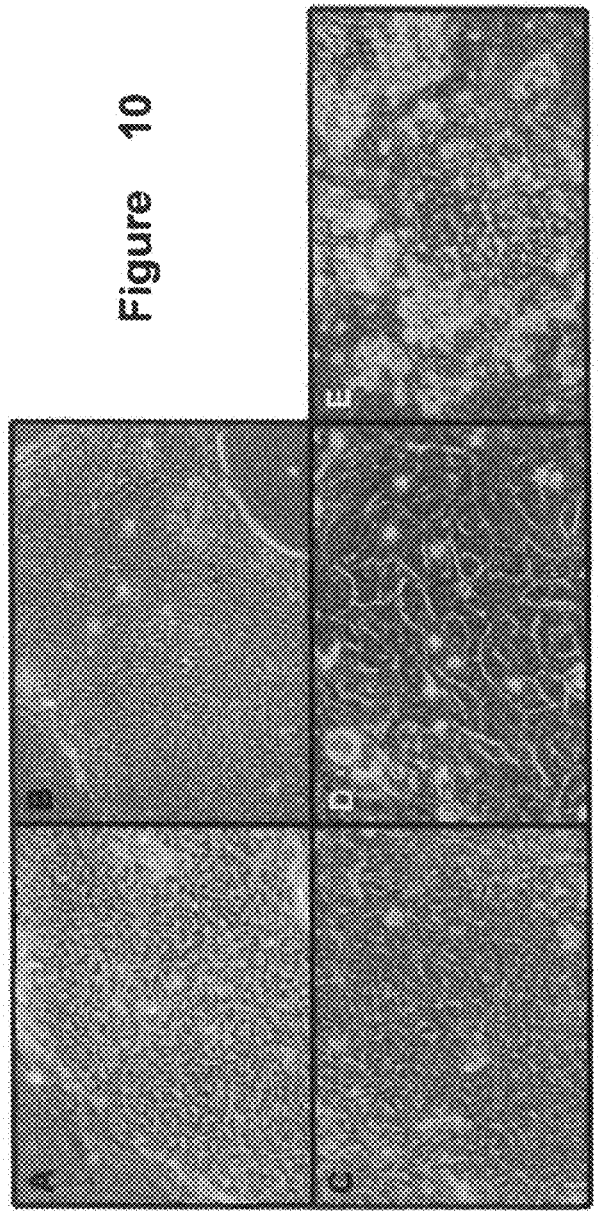
FIG. 10 shows the behavior of hHpSCs on substrata of purified matrix components: hHpSCs maintain stem cell characteristics on plastic or on type III collagen (A and B). hHpSCs lineage restrict to hepatoblasts when cultured on top of type IV collagen or on laminin (C and D). hHpSCs further differentiate into mature hepatocytes when cultured atop type I collagen. Higher magnification for D.

Type I collagen was determined to induce the most extensive differentiation. The extent of differentiation was found to differ depending on whether the cells were plated on top of or embedded into the type I collagen gel. Indeed, cells morphologically similar to mature hepatocytes were found in those cultures embedded in the collagen (FIG. 10). This phenomenon is likely due both to a direct effect of type I collagen and also an indirect effect via stabilization of HS-PGs by type I collagen.

Figure 11:
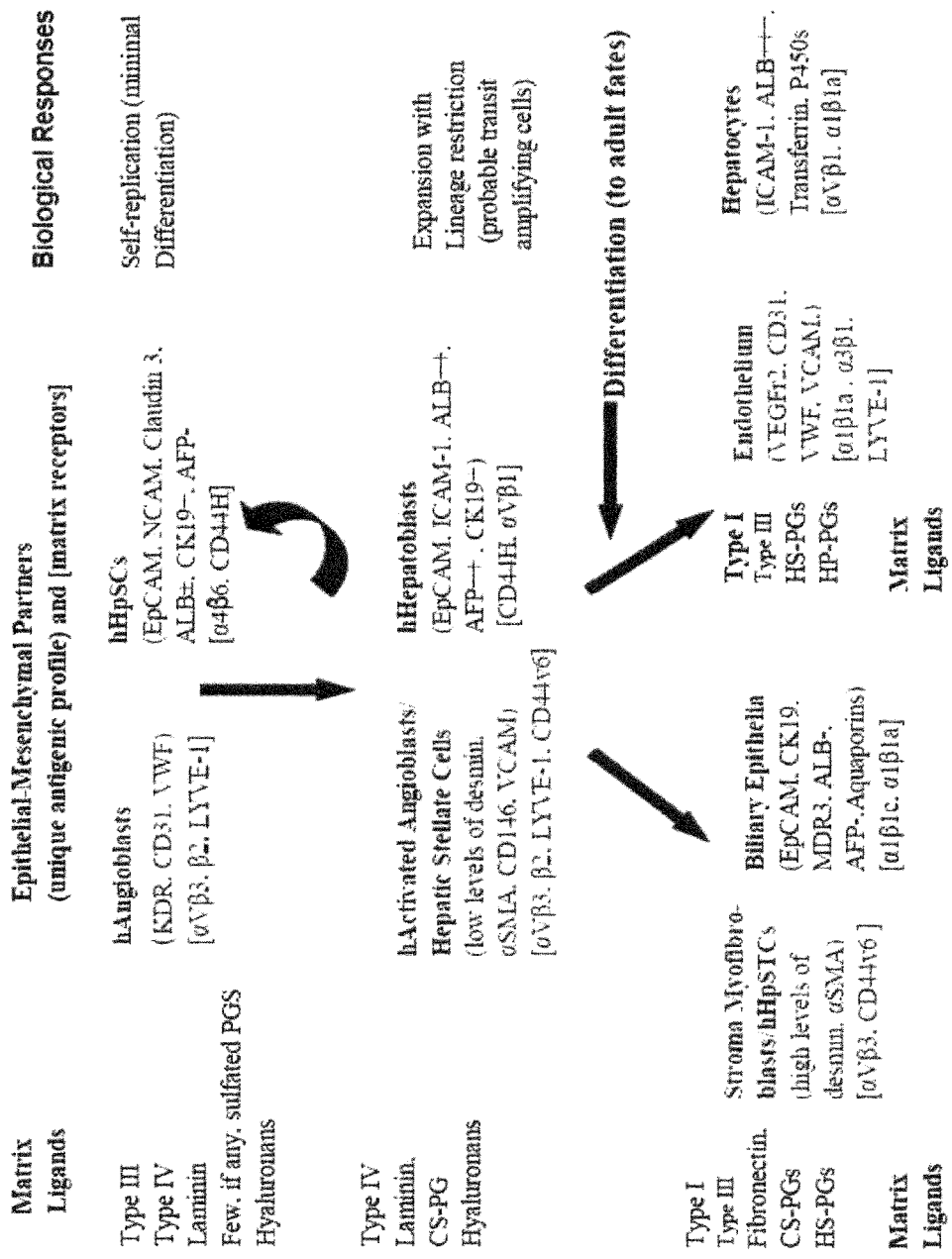
FIG. 11 provides a summary of the changes in matrix chemistry and matrix receptors in the hHpSCs and their mesenchymal cell partners during differentiation.

FIG. 11 summarizes the discovered sequential changes in matrix components and matrix receptors that occur with the transition of hHpSCs through hepatoblasts and ultimately to mature parenchymal cells. The invention thus defined can allow the propagation of HpSCs in "feeder-free" cultures. Table 2 provides details on the extracellular matrix components produced by different feeders studied.

and/or differentiation. For example, the addition of serum can slow growth of the hepatic progenitors and cause lineage restriction towards the hepatocytic fate and, in parallel, cause rapid expansion of mesenchymal cell populations (stroma and endothelia) associated with scar tissue formation. The addition of epidermal growth factor leads to lineage restriction towards an hepatocytic fate.

Preferably, in some embodiments, the matrix components described herein are employed in combination with a serum-free medium. A serum-free media was developed previously for HpSCs and hepatoblasts and is described in U.S. patent application Ser. No. 09/678,953, the disclosure of which is incorporated herein in its entirety.

TABLE 2

Extracellular Matrix Components Produced by Different Feeders

| | | | | | Human Fetal Liver Cells Immunoselected for: | | | |
|---|---|---|---|---|---|---|---|---|
| Matrix Components | | hHpSCs on plastic | hUVECs | hMSCs | CD31+ | KDR+ | Depletion of stroma | STO Cells |
| Collagens | Type I | Neg | | Neg | | | +/+ | +++ |
| | Type III | ++ | | | Neg | | | ++ |
| | Type IV | ++ | + | − | | ++ | | +++ |
| Adhesion Molecules | Laminin | + | − | − | + | + | + | ++ |
| | Fibronectin | Neg | | | Pos | | | +++ |
| Proteoglycans | Syndecan (HS-PG) | Neg | | | Neg | | | ++ |
| | Perlecan | Neg | | | Neg | | | ++ |
| | CS-PG | Neg | − | | + | − | − | + | +++ |
| GAGs | Hyaluronans | ++ | | | | | | |
| Functional Effects of Feeders on hHpSCs | | Self-replication; minimal, if any, differentiation | | Lineage restriction to hepatoblasts and with considerable expansion | | | | Growth arrest; differentiation |

GAGs = glycosaminoglycans.
The antibodies used were:
a set from Sigma (Sigma, St. Louis, MO): anti-human type I collagen mouse IgG1, anti-human type III collagen mouse IgG1, anti-human laminin mouse IgG1, anti-chondroitin sulfate mouse IgM. anti-human fibronectin mouse IgG1 (Oncogene Research Products, Cambridge, MA), rabbit anti-human type IV collagen IgG (Research Diagnostics Inc., Flanders, NJ), rat anti-human perlecan IgG2a (Lab Vision, Fremont, CA), anti-human syndecan
Controls: antibodies were screened against purified matrix components The scope of the present invention should not be limited to any one matrix component, soluble component, or combination thereof. In keeping with the teachings herein, the present invention describes and teaches the use of any and all soluble and insoluble components and their combination in the generation of substrata and media that can be utilized for ex vivo maintenance of cells either for expansion or for differentiation. While many of these components will be discussed below, for the sake of clarity, laminins, type IV collagens and/or type III collagens will be discussed as mere representatives of a class of extracellular matrix components that are found in or in high abundance in embryonic tissues or in stem cell niches.

Non-limiting examples of embryonic matrix components include: specific types of collagens, including Collagens Type IV (further including α1, α2, α3, α4, α5, α6) and Collagens Type III; Laminins (including, 1, γ1, β2, α3, α5); hyaluronans; forms of chondroitin sulfate proteoglycans (PGs) or their glycosaminoglycan chains; and forms of heparan sulfate-PGs or their glycosaminoglcyan chains (e.g., certain syndecans). Non-limiting examples of matrix components found in mature tissues include stable forms of collagens (e.g., type I and II), forms of fibronectin; heparan sulfate-PGs (e.g., agrin, perlecan), heparin-PGs; dermatan-PGs (e.g., cartilage-associated dermatan sulfate-PG); and elastins.

In addition to insoluble factors, soluble growth and/or differentiation factors can influence the rate of cell proliferation The present inventors have found that Interleukin-11 (IL-11) and leukemia inhibitory factor (LIF) promoted colony formation of rat hepatic progenitor (rter6) cells on top of STO feeders. Because both IL-11 and LIF are members of IL-6 cytokine superfamily, these findings support the notion that the IL-6 cytokine family promotes growth of hepatic progenitor cells in vitro. EGF reduced colony formation of rat hepatoblasts but increased colony formation of diploid adult rat hepatocytes but with lineage restriction towards hepatocytes and inhibition of biliary epithelia. As well, TGF-β1 increased colony number and area of rter6 cells when grown atop STO feeders, but inhibited growth of HepG2 cells on plastic.

Co-culture of hHpSCs and STO feeder cells induced higher expression of several human and mouse cytokines including in majority the inflammatory signals and some factors known to be hepatic growth stimulating. Interleukin-4 (IL-4) is one of the inflammatory cytokines that elevated dramatically in the co-culture. These and other soluble factors are discussed with greater detail herein.

Without being held to or bound by theory, it is presently believed that the matrix components and soluble components of the present invention provide many of the survival, proliferation and/or differentiation signals generally provided by feeder cells. Thus, the instant invention may replace, in significant part, the need for embryonic stromal feeder cells to maintain viability and expansion potential of the hepatic progenitors.

Embodiments of the instant invention will now be described by way of non-limiting examples.

EXAMPLES

Kubota's Medium (KM)

All cultures were put into KM, a serum-free medium (unless otherwise noted) tailored for hepatic progenitors. The media is described in, for example, U.S. patent application having Ser. No. 09/679,663 filed Oct. 3, 2000, the disclosure of which is incorporated herein in its entirety by reference.

Sourcing of Cell Lines hMSCs were obtained from a 26-year-old male donor. hUVECs were obtained from Dr. Cam Patterson (University of North Carolina; Chapel Hill, N.C.). A clone of murine embryonic stromal cells (STO cells) was prepared from STO cells obtained from the ATCC.

Sourcing of Human Liver Tissue

Human fetal livers, 16-20 weeks gestational age, were obtained from Advanced Biological Resources (ABR, San Francisco, Calif.).

Isolation and Culture of hHpSCs

Human fetal livers were processed as noted, supra. Freshly isolated parenchymal cells were placed into KM and culture plastic or atop pre-plated feeders of hUVECs, hMSCs, STO cells, or primary cultures of human fetal liver-derived cells at a plating density of 5,000 cells/cm$^2$. The cells were in KM plus 2% FBS overnight and then switched to KM thereafter. The cultures on plastic and in KM yield colonies of hHpSCs surrounded by angioblasts and hHpSTC precursors that were not activated.

Preparation of Feeders

All stocks of mesenchymal feeders were cultured on culture plastic and in Endothelial Growth Medium, (EGM-2) (Cambrex, Walkersville, Md.) with 2% FBS. The only exceptions to these conditions were the hMSCs and the adult liver-derived HpSTCs, which were grown as described below. All cells were grown to confluence, growth arrested with Mitomycin-C, and then switched to KM for use in co-cultures with hHpSCs. Further details follow:

hMSCs were plated onto tissue culture dishes with DMEM plus 1% antibiotics, ascorbic acid, 2 mM L-glutamine and 10% FBS.

Purified preparations of HpSTCs from adult rat and adult human livers were prepared by Dr. YiWei Rong. The stocks of feeders were cultured on plastic and in KM+5% FBS.

STO5 feeders were cloned from STO cells obtained from the ATCC and were tested for their efficacy on rodent hepatic progenitors. Frozen stocks of STO5 were thawed and grown in KM to which 5% fetal bovine serum was added.

For preparation of primary cultures of human fetal liver-derived mesenchymal cells, livers were enzymatically digested using 0.45 mg/ml collagenase type IV and 0.3 mg/ml deoxynuclease and then mechanically dissociated into single cell suspensions by cross scalpels. After washing away excess enzymes, the cells were put through three rounds of slow-speed centrifugation (20×g) for 5 minutes. The supernatant was collected and resuspended in RPMI-1640 plus selenium ($10^{-9}$M), 1% antibiotics and 0.1% BSA. The cells were then plated onto culture plastic and in KM supplemented with 10% FBS. The mesenchymal cells attached within minutes to hours and quickly transitioned into stromal feeders comprised of activated hHpSTCs recognizable by having high levels of desmin, CD146 and αSMA.

KDR+ or CD31+ cells were isolated from the fetal liver cell suspensions by magnetically activated cell sorting (MACS) system using monoclonal anti-human KDR mouse IgG1 (Cell Sciences, Canton, Mass.), goat anti-mouse IgG coupled to magnetic microbeads or using monoclonal anti-human CD31 mouse IgG1 conjugated to magnetic microbeads. Plating density for KDR+ and CD31+ cells was 20,000 cells/cm$^2$.

Feeders depleted of stromal cells were prepared by negative selection for fibroblasts using monoclonal anti-human fibroblast mouse IgG2a conjugated to magnetic microbeads according to manufacturer's instructions (Miltenyi Biotec, Auburn, Calif.). The plating density for fibroblast-depleted supernatant cells was 500,000 cells/cm$^2$.

Purified Matrix Substrata

The preparation of matrix substrata for in vitro culture is described in U.S. patent application having Ser. No. 11/560,049 filed Nov. 15, 2006, the disclosure of which is incorporated herein in its entirety by reference.

Fibronectin: Fibronectin (Sigma, F0895) was coated onto dishes at concentrations of 0.5, 1.0, or 2 μg/cm$^2$ and then neutralized to pH 7.4.

Laminin: Laminin (Sigma, L2020) was coated onto dishes at concentrations of 0.52 or 1.0 μg/cm$^2$ at pH 7.4.

Collagen, types III and IV: Collagen coatings were prepared on dishes at 1 of 5 different protein concentrations (2.1, 4.2, 6.3, 8.3, and 10.4 μg/cm$^2$). Matrix components were added in acidic buffers to the dishes. The matrix was allowed to attach over a 10-hour period at 37° C. and 5% CO$_2$. After 10 hours, the dishes were sterilized by UV irradiation for 2-hours and then rinsed 3× with PBS. Collagen III (Sigma, C-3511) was formed with pH 3 acetic acid and Collagen IV (Sigma, C-5533) with 0.5M acetic acid.

Collagen, type I: Vitrogen 100 (Cohesion Technologies, Palo Alto, Calif.) was modified into liquid collagen type-I by adding specific ratios of 10×DMEM and 0.1 M NaOH. Because air bubbles can make gels unstable, the formation of air bubble formations was prevented. The collagen I was used both for monolayers of cells or as a "sandwich" to embed cells between two layers of collagen.

Monolayers of Cells on Collagen I: Liquid collagen I was maintained at 4° C. prior to distributing 0.4 ml into each well of a 6-well plate. After coating, the collagen was gelled at 37° C. and 5% CO$_2$ for 1-hour.

Sandwich (Embedded cells) Model: Cells were sandwiched between layers of collagen. After a 10-hour period for cell attachment period, unattached cells were removed, and a second 0.4 ml layer of collagen I added. The system was allowed to gel at 37° C. and 5% CO$_2$ for 1 hour to solidify the top collagen layer.

Immunohistochemistry on Human Hepatic Progenitor Cells and Human Fetal Liver-Derived Feeder Cells After 1-2 weeks of culture, cells were fixed with 4% paraformaldehyde for immunostaining. A antibodies used were as follows: FITC-conjugated anti-human vWF sheep IgG (US Biologicals, Swampscott, Mass.), PE-conjugated anti-human CD56 (NCAM) mouse IgG1, anti-human CD31 mouse IgG1, PE-conjugated anti-human CD54 (ICAM-1) mouse IgG1 (BD, San Jose, Calif.), anti-human αSMA mouse IgG2a, anti-human type I collagen mouse IgG1, anti-human type III collagen mouse IgG1, anti-human laminin mouse IgG1, anti-chondroitin sulfate proteoglycan mouse IgM (Sigma, St. Louis, Mo.), anti-human fibronectin mouse IgG1 (Oncogene Research Products, Cambridge, Mass.), rabbit anti-human type IV collagen IgG (Research Diagnostics Inc., Flanders, N.J.), rat anti-human perlecan IgG2a (Lab Vision, Fremont, Calif.), rabbit anti-human AFP IgG (Zymed-Invitrogen, South San Francisco, Calif.), anti-human KDR mouse IgG1 (Cell Sciences, Canton, Mass.), Alexa Fluor 488 goat anti-rabbit IgG, Alexa Fluor 568 goat anti-rabbit IgG, Alexa Fluor 568 goat anti-mouse IgG1 and Alexa Fluor 488 goat anti-mouse IgG2a (Molecular Probes-Invitrogen, Eugene, Oreg.).

Quantitative Real-Time PCR

Total RNA was extracted from cells using RNeasy® Mini (Qiagen, Valencia, Calif.). The extracted RNA was then reverse-transcribed into cDNA using SuperScript® II RT (Invitrogen, Carlsbad, Calif.). Real-time quantitative PCR was performed using sequence specific primers and probes shown in the Table 3 below and analyzed by the ABI Prism 7000 Sequence Detection System (Applied Biosystems, Foster City, Calif., USA). Ribosomal RNA (18S) from each cell type was used as internal control. The mRNA expression levels relative to 18S were determined and the fold changes were calculated using the $2^{-\Delta\Delta C_T}$ method. Primers used are tabled below:

TABLE 3

PCR primers

| Genes | ABI assay number |
| --- | --- |
| Ribosomal RNA (18S) | 4308329 |
| type I collagen-α1 chain (COl1A1) | Hs00164004__m1 |
| type III collagen-α1 chain (COL3A1) | Hs00164103__m1 |
| type IV collagen-α1 chain (Col4A1) | Hs00266237__m1 |
| type V collagen-α1 chain (COL5A1) | Hs006090088__m1 |
| fibronectin module 1 (FN1) | Hs01549972__m1 |
| laminin-α2 chain (LAMA2) | Hs00166308__m1 |
| laminin-α4 chain (LAMA4) | Hs00158588__m1 |
| laminin-α5 chain (LAMA5) | Hs00245699__m1 |
| laminin-β1 chain (LAMB1) | Hs00158620__m1 |
| laminin-γ1 chain (LAMC1) | Hs00267056__m1 |
| syndecan-1 (SDC1) | Hs00174579__m1 |
| syndecan-2 (SDC2) | Hs00299807__m1 |
| glypican-3 (GPC3) | Hs00170471__m1 |
| glypican-5 (GPC5) | Hs00270114__m1 |

"Native" Feeder Cells for hHpSCs

Figure 2:
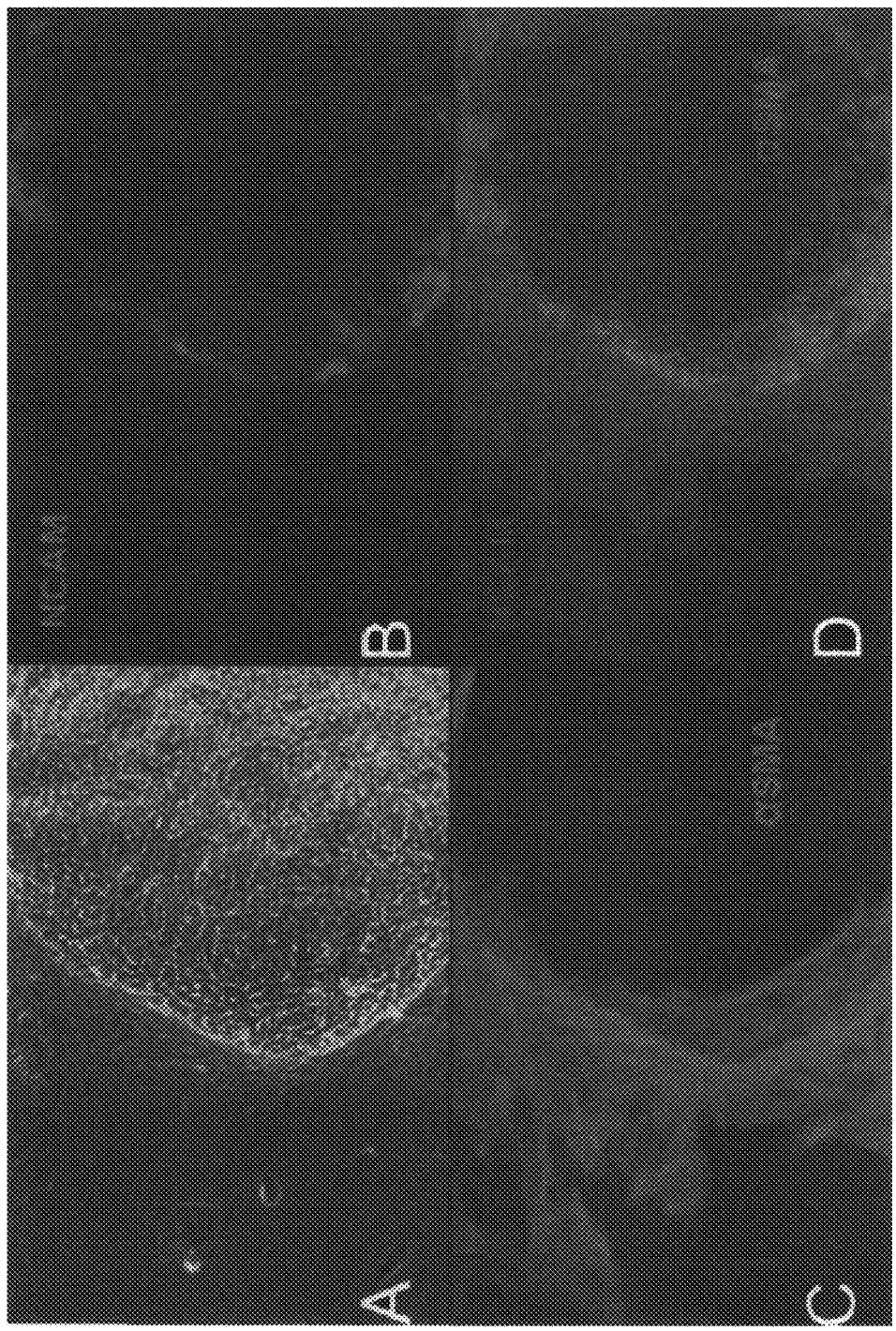
FIG. 2 shows that cells surrounding a colony of hHpSCs are αSMA+hHpSTCs: A typical human hepatic stem cell colony (A) is positive for NCAM inside the colony (B, D) and for αSMA in the companion cells at the edge of colony (C, D). Magnification, 10×.
Figure 3:
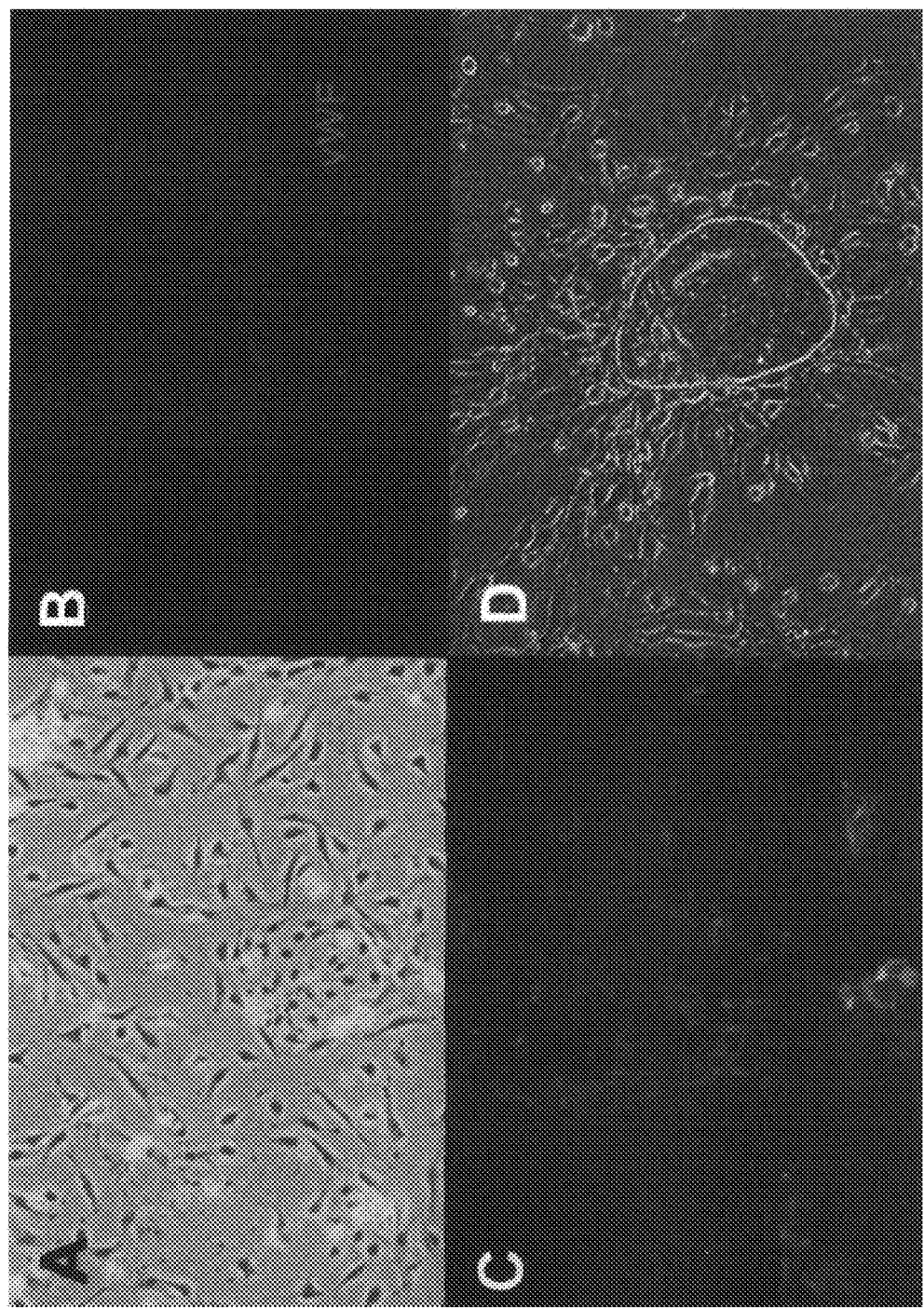
FIG. 3 shows a primary culture of hHpSCs with angioblasts: KDR+ selected cells cultured in EGM-2 for 7 days expressed vWF (green) (A and B). CD31+ selected cells cultured in EGM-2 for 4 days expressed both vWF (green) and CD31 (red) (C). Scale bar, 100 µm. Angioblasts associated with hHpSC colony in culture (D). Magnification, 10×.

Freshly isolated hHpSCs survived ex vivo on tissue culture plastic in KM, when the cells were in the presence of angioblasts (VEGFR2+, CD31+, CD133/1+, CD117+) and quiescent hHpSTCs (CD146-low, desmin and αSMA) (FIGS. 1-3). Colonies of hHpSCs consisted of cells tightly bound to each other on their lateral borders but with minimal attachment to the culture dish per se. However, at the perimeter of the colonies, the site at which the angioblasts cells were located, the hHpSCs attached to the dish. Thus, attachment was either by the mesenchymal companion cells (e.g., the angioblasts) alone or in combination with hHpSCs.

Feeder Cell Lines and Feeder Primary Cells Used to Model the "Native" Feeders

Several forms of embryonic mesenchymal cells, either primary cultures or cell lines, were prepared as models of "native" feeders (e.g., angioblasts and HpSTCs). hHpSCs were cultured on these feeder cells in KM. While minimizing exposure to serum is essential to stave off spontaneous differentiation of hHpSCs, mesenchymal feeders require factors from serum for survival. To overcome this technical hurdle, the present inventors grew stocks of mesenchymal feeders in medium, such as EGM-2, supplemented with 2% serum before switching to serum-free medium, such KM, for assays requiring co-culture of feeders and hHpSCs.

Figure 4:
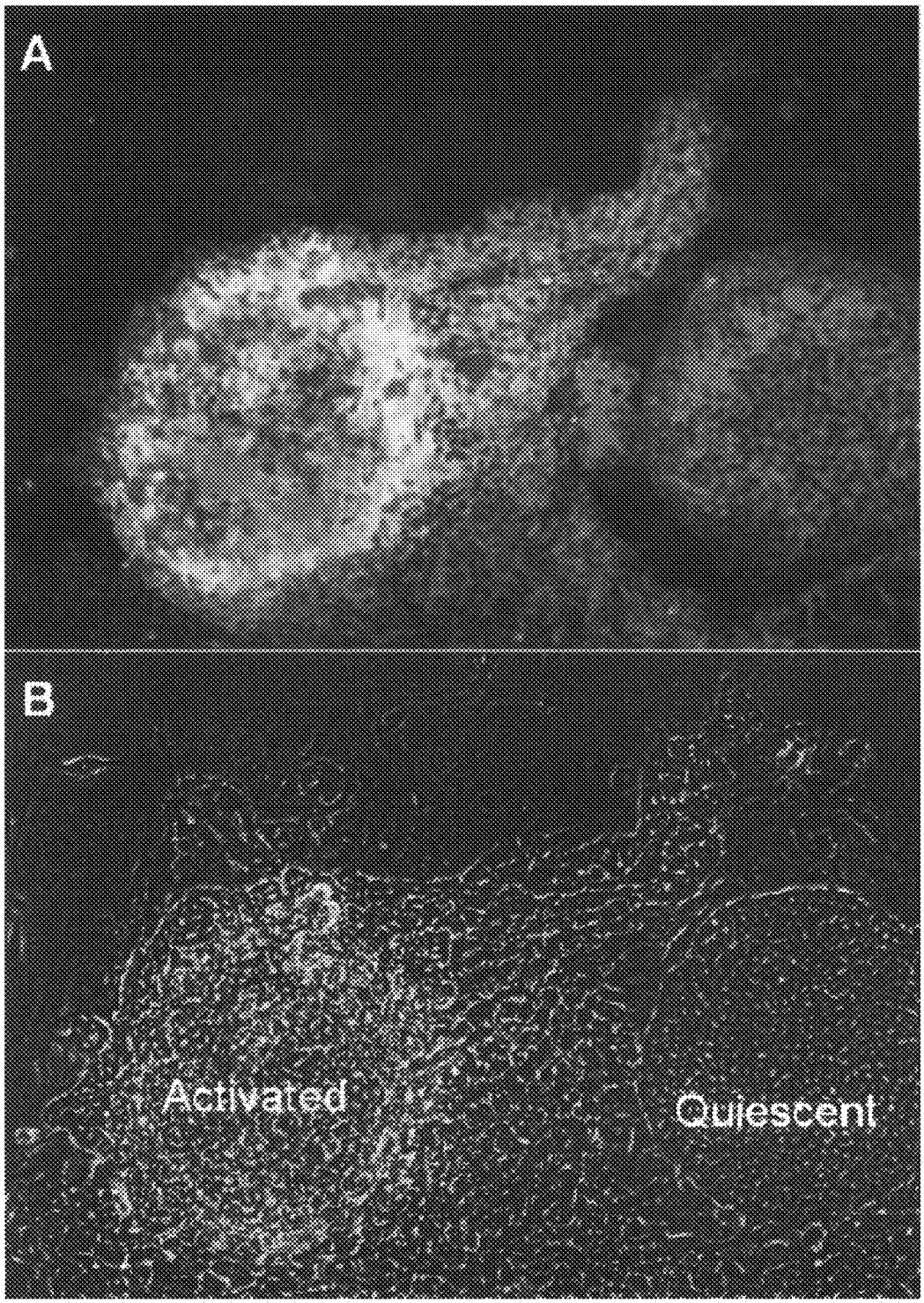
FIG. 4 compares quiescent with activated hHpSTCs: Quiescent hHpSTCs express low levels of desmin, αSMA+, CD146, type I collagen, and other matrix molecules (fibronectin, proteoglycans). Injury processes—for example, exposure to serum or to certain factors (e.g., PDGF and TGF-B1)—cause hHpSTCs to activate and to transition to myofibroblast-like stromal cells and elevate production of αSMA and matrix components, and to release various growth factors such as HGF. Shown is a colony of hHpSCs encircled by mesenchymal companion cells (angioblasts and quiescent hHpSTCs) expressing low levels of CD146. On the same plate, an adjacent colony is shown with the mesenchymal companion cells that have undergone activation resulting in high levels of CD146.

When maintained in serum-free medium (FIGS. 1-3), hHpSTCs were found to be quiescent, expressing low levels of CD146, desmin and αSMA. Upon exposure to serum, however, even at low (1-2%) levels or for 5 days, resulted in activation of the hHpSTCs as evidenced by high levels of CD146, desmin and αSMA (FIG. 4). Exposure to serum also induced primary cultures of fetal liver cells, or immunoselected cells (i.e., KDR+ or CD31+ cells, discussed hereinbelow), to differentiate into hHpSTCs.

Feeder cell lines tested were: hMSCs (FIG. 5A), hUVECs (FIG. 5B), and murine embryonic stromal cells (STO), often used for maintenance of ES cells in culture. Primary cultures were prepared from cell suspensions of 16-20 week-old human fetal livers by immunoselection. Cells expressing KDR (a.k.a. flk-1/VEGFR2) or CD31 (a.k.a. PECAM), or cells that remain upon negative sorting for fibroblasts thereby reducing or eliminating stromal cells were selected by MACS. Whole livers comprised 0.5% and 1% KDR+ and CD31+ cells, respectively. These immunoselected populations of cells were cultured in EGM-2 medium.

Figure 5:
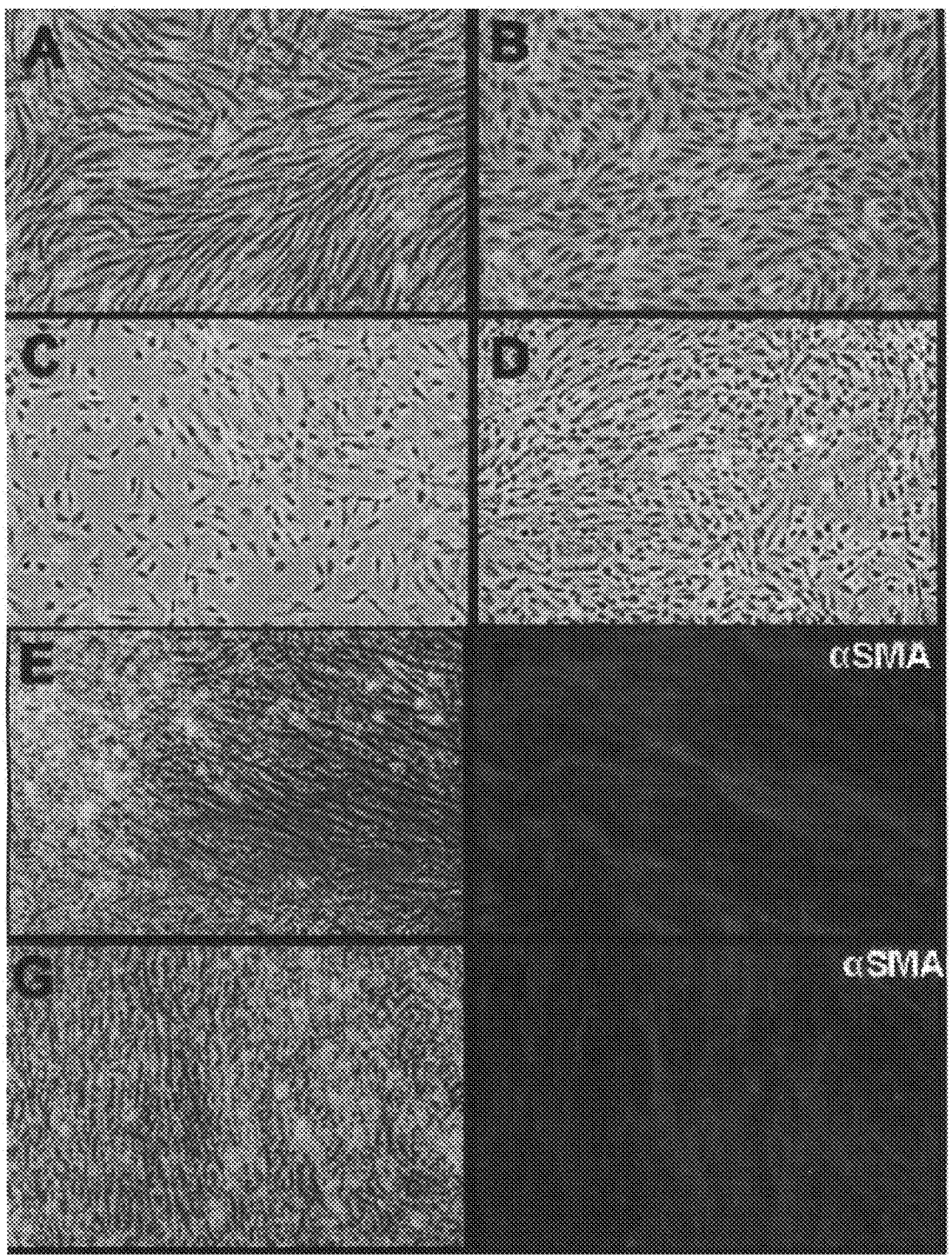
FIG. 5 shows the morphology and immunohistochemistry of different feeders: A: hMSCs. B: hUVECs. C-D: human fetal liver-derived feeder cells on days 4 (C) and 7 (D). E-H: day-11 culture of magnetically immunoselected KDR+ cells (E-F) and supernatant cells depleted of fibroblasts (G-H) in serum-free conditions were positive for αSMA (F and H). Magnification, 10×.
Figure 6:
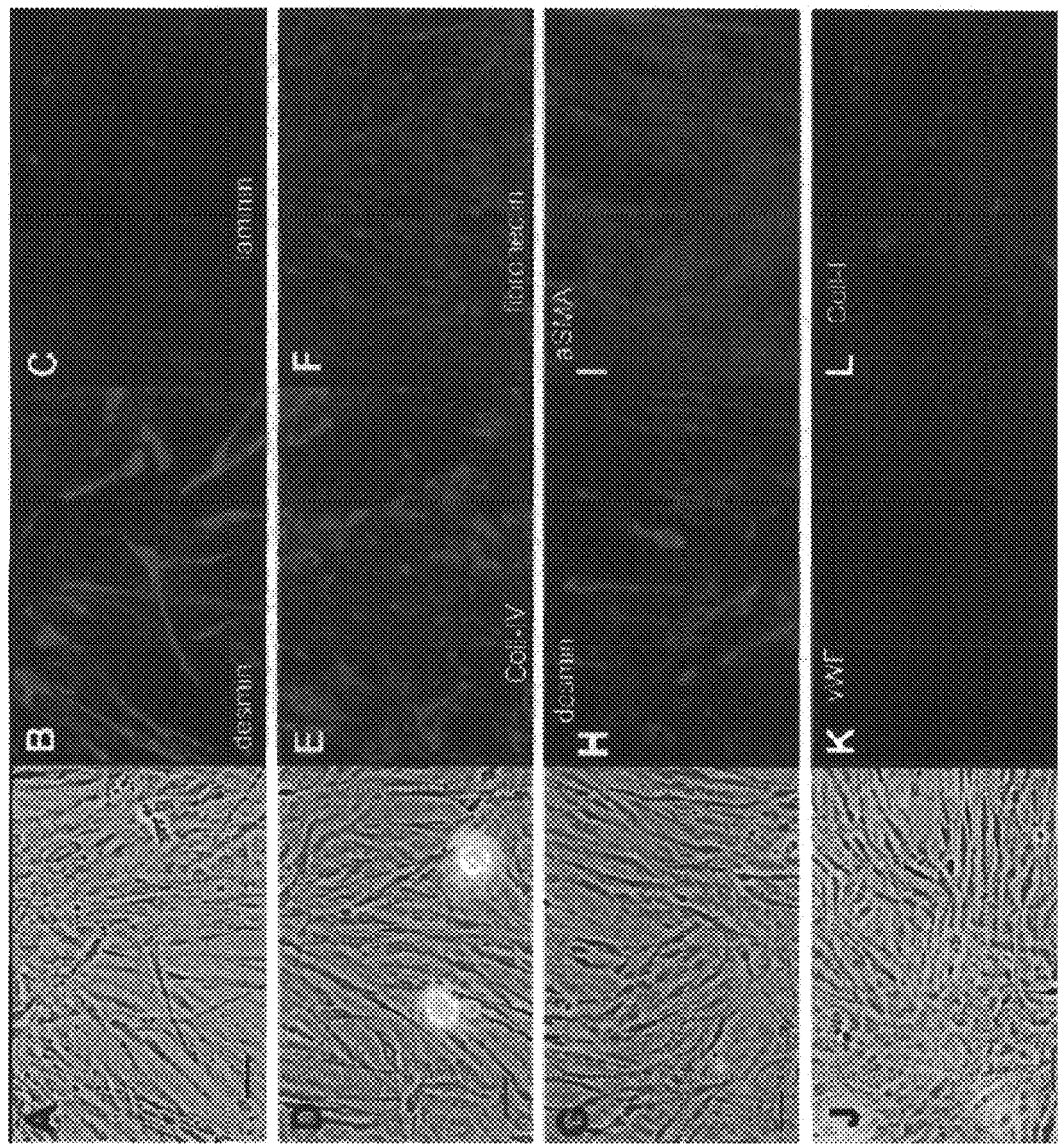
FIG. 6 shows immunohistochemistry on fibroblast-depleted supernatant cells cultured in EGM-2 medium for 8 days: Cells were positive for desmin (B and H), αSMA (I), laminin (C), fibronectin (F), collagen types I (L) and IV (E), and negative for endothelial marker vWF (K). Note that more cells express αSMA than desmin. Phase contrast image for each double staining is shown (A, D, G, and J). Bar, 50 µm.

Immunoselected KDR+ cells changed rapidly in culture. In the first week, the cells morphologically and antigenically appeared as angioblasts or endothelial cells (FIG. 3D). By the second week, however, HpSTCs dominated the culture. Indeed, the cultures were confluent at 11 days, and most of the cells were positive for αSMA, a marker for hHpSTCs and negative for vWF, an intracellular marker for endothelial cells (FIGS. 5F and H and 6I and K). Even if the cell suspension was negatively fractionated to eliminate stroma prior to plating, the same phenomenon was observed (FIGS. 5C-E and G).

CD31+ cells appeared as cobblestone-like cells in morphology for the first five days in culture and were positive vWF, indicating that the cells were endothelial cells. After 5-7 days of culture, however, hepatic stellate cells (strongly expressing αSMA and desmin) dominated the dish and quickly reached confluency by day 9-10. The results demonstrate that EGM-2, though specifically designed for endothelial cells is nevertheless permissive for outgrowth of hHpSTCs.

hHpSCs on Feeders of Angioblasts or hUVECs Remain as Stem Cells

Figure 7:
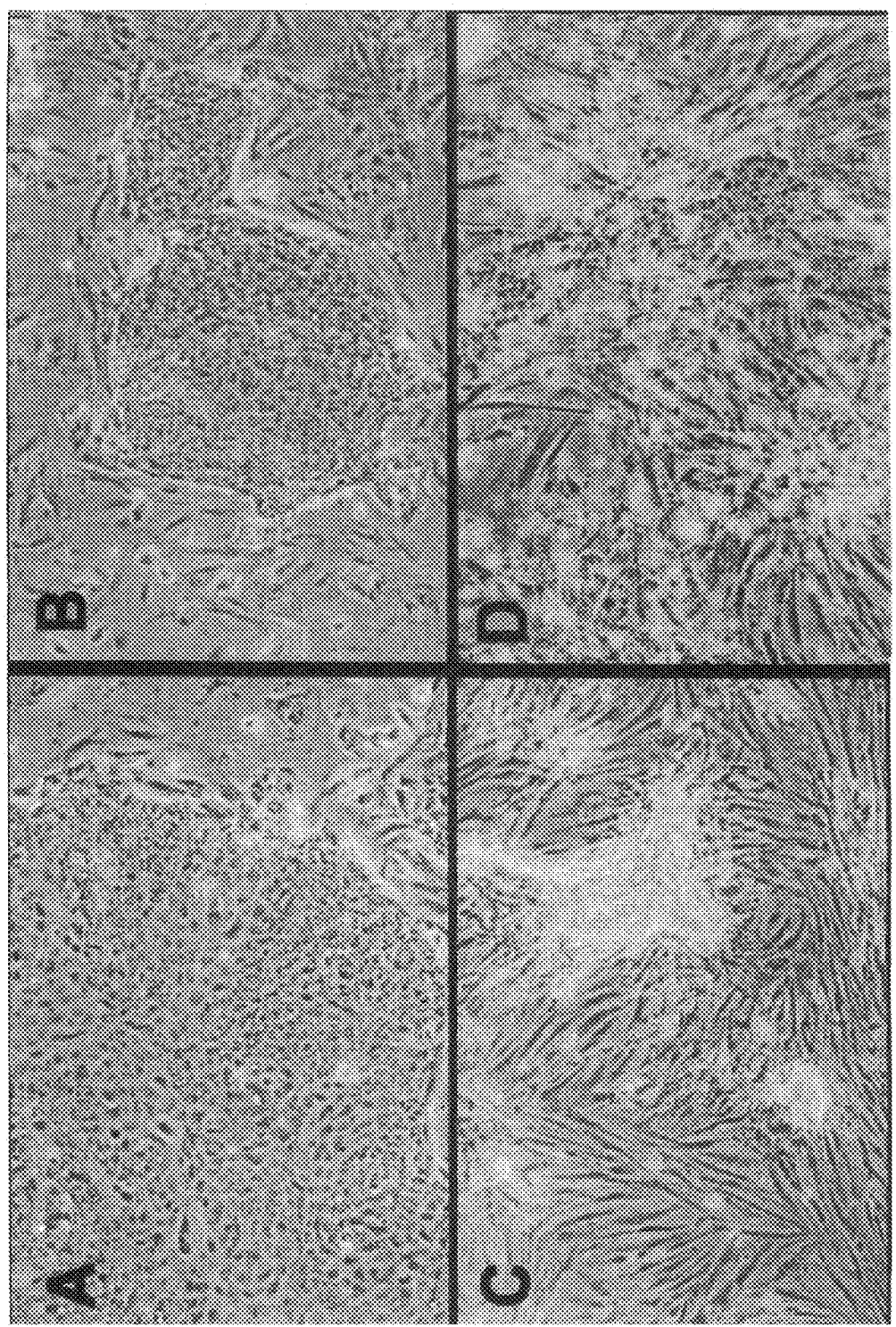
FIG. 7 shows some effects of hHpSCs co-cultured with different feeders. A-F: hHpSCs cultured alone (A), co-cultured with hUVECs (B), hMSCs (C), or human fetal liver-derived feeders (D). Magnification, 10×.
Figure 8:
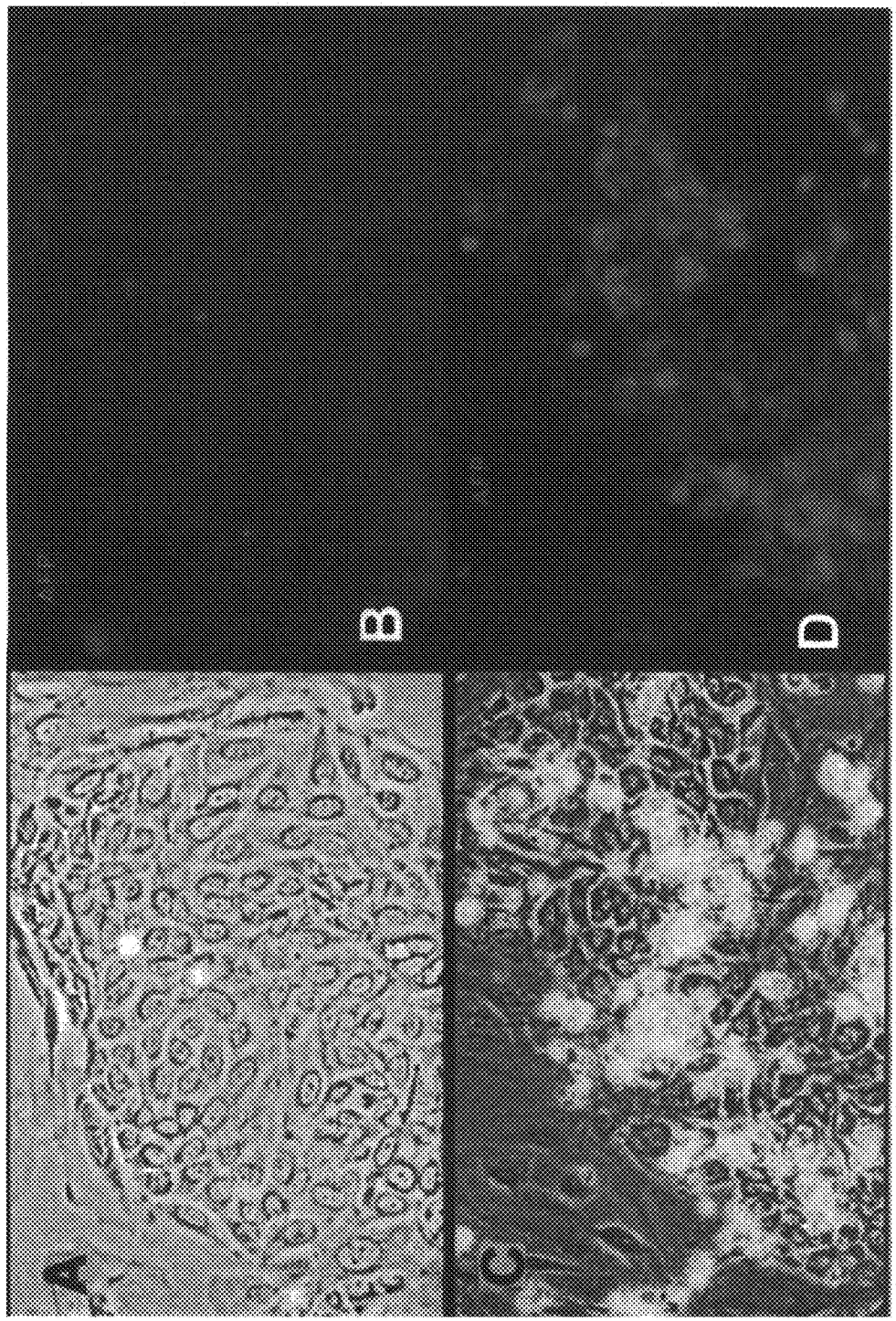
FIG. 8 shows human hHpSCs co-cultured with αSMA+ supernatant cells derived from human fetal livers, from which fibroblasts were depleted. Use of these feeders resulted in lineage restriction to hepatoblasts. Immunohistochemistry for human AFP on human hepatic stem cell colonies (A and B) and on co-culture of hHpSCs and human fetal liver-derived feeders (C and D) at day 8. Magnification, 10×.

Isolation and clonogenic expansion of hHpSCs on culture plastic and in KM in which there was close association with angioblasts and quiescent HpSTCs resulted in cells that remained as hHpSCs with minimal differentiation (FIG. 3). The hHpSC colonies can be seen 2 weeks after plating and are positive for NCAM, EpCAM, albumin, CK19 and CLDN-3 and negative for AFP. hHpSCs cultured in KM and atop hUVECs or on KDR+ feeder cells immediately after sorting also maintained hHpSCs as stem cells (FIG. 7B) with an antigenic profile of EpCAM+, NCAM+, ICAM-1−, AFP−, CLDN-3+.

hHpSCs cultured on feeders of activated hepatic stellate cells lineage restrict to hepatoblasts hHpSCs cultured on activated hHpSTCs caused rapid transition, within hours, of hHpSCs to hepatoblasts (FIG. 4). hHpSCs cultured on either hMSCs; primary human fetal liver stroma cells; primary human fetal liver stroma cells depleted of fibroblasts; primary KDR+ cells; or primary CD31+ cells also transitioned to hepatoblasts after more than a week in culture. After 8-9 days of co-culture with any of these feeders, the hepatic progenitor colony morphology consisted of cord-like structures interspersed with clear channels, the presumptive biliary canaliculi (FIGS. 7 and 8) and with an antigenic profile indicative of hepatoblasts (EpCAM+, NCAM−, ICAM-1+, AFP+) (FIG. 1). Moreover, the morphology of hepatoblast colonies was more 3-dimensional causing them to be refractile when evaluated by bright field (FIGS. 7 and 8) possibly caused by multiple layers of cells and/or accumulation of extracellular matrix.

hHpSCs Plated onto STO Feeders

The feeder model system resulting in the maximum differentiation proved to be STO feeders. hHpSCs plated onto these feeders significantly slowed their growth and then gave rise to hepatoblasts and committed progenitors from the edges of the colonies.

Gene Expression of Matrix Molecules by the Feeders

Figure 9A:
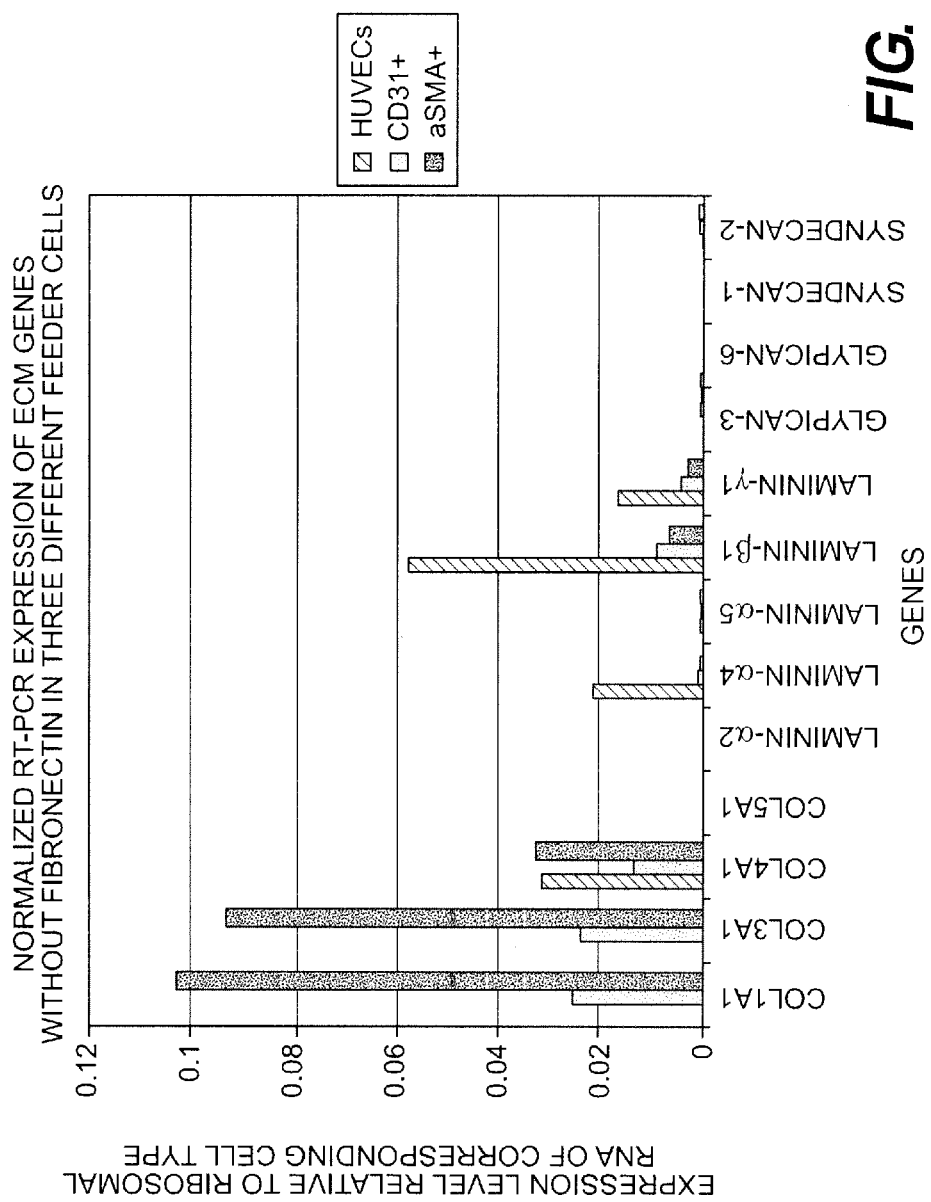
FIG. 9 shows normalized mRNA expression for mRNAs encoding matrix molecules: fold changes of mRNA expression levels in each cell type were normalized to ribosomal RNA (18S) content of the same cell type.
Figure 9B:
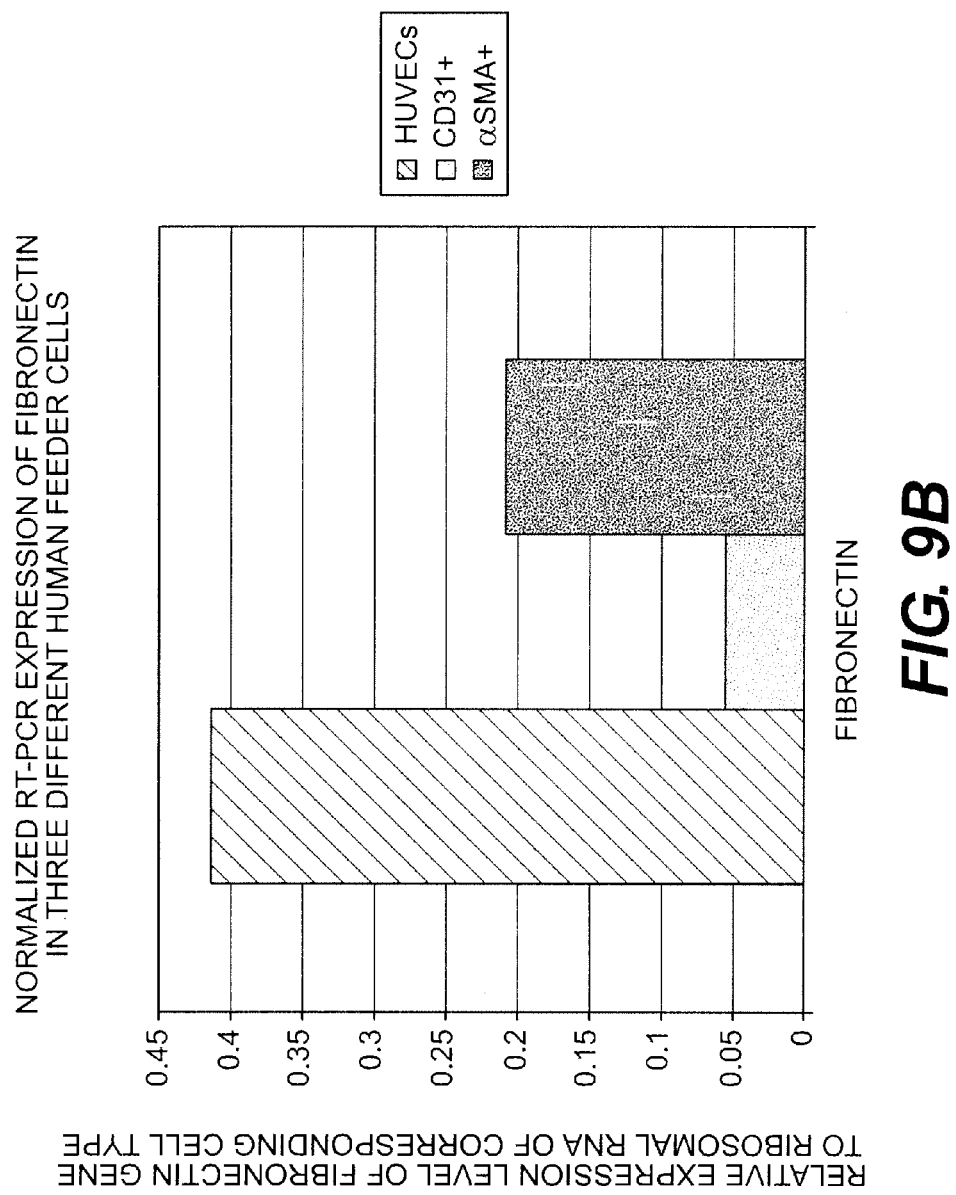

Three feeder cell types were chosen to represent feeders that either sustained the hHpSC phenotype (hUVEC cells); caused differentiation to hepatoblasts (primary cultures of human fetal liver mesenchymal cells and CD31+ cells); or lead to more advanced differentiation down the hapatocytic pathway (fetal liver-derived endothelia cultured for more than a week, both assayed at time points at which hHpSTCs were the dominant cell population). Using real time PCR, it was found that fibronectin mRNA encoding the type I module of the fibronectin molecule was the highest-expressed matrix component among the three feeders assayed, especially in hUVECs (FIG. 9). The hUVEC feeders, supportive of maintenance of the hHpSC phenotype produced collagen type IV, laminin ($\alpha 4$, $\beta 1$ and $\gamma 1$ chains), and little or no collagen types I and III, laminin chain isoforms other than those aforementioned, or proteoglycan core proteins. Those that induced lineage restriction to hepatoblasts (human fetal liver-derived $\alpha$SMA+ fibroblast-like and CD31+ cells) produced type I, III and IV collagen, laminin ($\beta 1$, $\gamma 1$), but not collagen type V, other laminin chains or any of the proteoglycan core protein genes assayed (Glypican-3 and -5 and Syndecan-1 and -2).

Protein Expression of Matrix Molecules by the Feeders

Immunohistochemistry (IHC) was performed on the feeders for 7 different matrix molecules: type I, III and IV collagens, laminin, fibronectin, and heparan sulfate proteoglycans (HS-PG) (i.e., perlecan and syndecan) and chondroitin sulfate proteoglycans (CS-PG). All feeders produced a mix of extracellular matrix molecules, but the lowest levels of total matrix molecule production were found in primary cultures of angioblast/endothelia; followed by the hUVEC cell line or primary cultures in which hHpSTCs had been culture selected. The highest level of matrix molecules were produced by STO cells. The basal adhesion molecule, fibronectin, was found in all of the feeders and with the highest levels found in STO cells. Interestingly, collagen type III was found expressed only in STO cells, whereas it was found in other feeders by RT-PCR.

Without being held to nor bound by theory, hHpSCs maintain their phenotype when cultured on an extracellular matrix containing forms of laminin with integrins $\alpha 4$ and $\beta 6$, type IV collagen, CS-PG, and no HS-PGs. Matrices that induce lineage restriction to hepatoblasts have elevated levels of type I, III and IV collagens, laminin (no $\alpha 4$ and no increase in the $\beta 1$ isoform), CS-PG and no HS-PGs. Finally, matrices that induce the most striking differentiation (i.e., beyond the hepatoblasts stage) also have all of the matrix components mentioned but levels higher than observed among other feeders. These matrices, however, were unique in containing HS-PGS (FIG. 11).

Effects of Purified Matrix Molecules on hHpSCs Versus Hepatoblasts hHpSCs were cultured in KM and on each of the following 5 types of matrix components coated onto plastic dishes: fibronectin, laminin and type I, III or IV collagen. Few of the hHpSCs cells attached to fibronectin, and those that attached did not grow. hHpSCs lineage restricted to hepatoblasts if cultured on laminin and/or type IV collagen or if plated on a surface of type I collagen gel (FIG. 10). When embedded into type I collagen, the hHpSCs differentiated the most, with the morphology and antigenic profile of the colonies resembling that of mature hepatocytes.

Matrix components within the periportal zone and in the liver's stem cell niche are distinct from those found in association with the mature parenchymal cells and elicit distinct biological responses from purified subpopulations of human hepatic stem/progenitor cells. These differences are likely to provide diverse signals that modify cell responses and activate dynamic expressions. By determining how distinct classes of extracellular matrix components induce in vivo and in vitro cell activities, microenvironments can be reproduced in vitro to expand and differentiate HpSC populations for the replacement or repopulation of diseased tissues.

In addition to matrix proteins, feeder cells are thought to provide soluble factors (e.g., cytokines, growth factors) that are essential for HpSC survival, proliferation, and/or differentiation. Non-limiting examples of relevant factors are listed below:

| | |
|---|---|
| Eotaxin (human and mouse) | Eotaxin: encoded by the CCL11 gene in human (Ccl11 in mouse), known to attract eosinophils in the presence of allergens. |
| G-CSF (mouse) | Granulocyte Colony Stimulating Factor. Encoded by the mouse gene csf3, expression this 208 aa protein is known to stimulates the growth and differentiation of hematopoietic precursor cells from granulocytes, macrophages, eosinophils and erythrocytes lineages. |
| GM-CSF (human and mouse) | Granulocyte-Macrophage Colony-Stimulating. Encoded by the CSF2 gene in human, (csf2 in mouse) this protein is indispensable for the growth and development of progenitors of granulocytes and macrophages, and triggers the irreversible differentiation of myeloblasts and monoblasts. |
| HGF (human) | Hepatocyte Growth Factor. Encoded by the human gene HGF (give rise to the 728 aa precursor) HGF is a growth factor for a broad spectrum of tissue and cells. HGF is involved in the maturation of liver stem cells. |
| IFN-$\gamma$ (human and mouse) | Interferon gamma. Encoded by the human gene IFNG (mouse Ifng), IFN-$\gamma$ is a dimeric protein which comprises six naturally occurring variants forms. In addition to its immunomodulatory activities, IFN-$\gamma$ is a growth-promoting factor for T-lymphocytes and a growth inhibitor for IL-4 induced B-cells, smooth muscle cells and endothelial cells. It functions as an inhibitor of capillary growth mediated by myofibroblasts, fibroblast growth factors and PDGF. |
| KC (Mouse) | Keratinocyte Chemoattractant. The new designation for KC is CXCL1 and the gene symbol is Cxcl1. KC is involved in chemotaxis and cell activation of neutrophils. In vitro it inhibits hematopoietic progenitor cell proliferation. A natural N-terminally truncated form (4 amino acids) can be isolated from bone marrow stromal cells. This factor augments the formation of Granulocytes-Macrophage Colonies Forming Units in the presence of other colony stimulating factors. Compared with full-length KC, the shortened factor is approximately 10 million times more potent as synergistic growth stimulant for GM.CFU. |
| IL-1Ra (human) | Interleukin 1 receptor antagonist. Encoded by the IL1RA gene The 152 aa secreted protein and the 177 intracellular forms antagonize IL-1 by binding to the IL-1 receptor. |
| IL-1$\alpha$ (human) | Interleukin 1 alpha. Encoded by the gene IL1A, the 271aa precursor is processed by a highly regulated mechanism to a159 aa secreted protein. IL1 in combination with other cytokines is an |

| | |
|---|---|
| | important mediator of inflammatory reactions. in fibroblasts, synovial cells, chondrocytes, endothelial cells, hepatocytes, and osteoclasts. IL1 acts directly on B-cells, promoting their proliferation as well as that of fibroblasts, thymocytes, and glioblastoma cells. IL1 inhibits the growth of endothelial cells in vivo. In vascular smooth muscle cells and skin fibroblasts IL1 induces the synthesis of bFGF which is a mitogen for these cells. |
| IL-1β (human and mouse) | Interleukin 1 beta. Encoded by the human gene IL1B (mouse gene Il1b). The Activities or IL1-beta are similar to IL1alpha. |
| IL-2 (human and mouse) | Interleukin 2. This protein, encoded by human gene IL2 and mouse gene Il2 induces clonal expansion of Tcells. |
| IL-4 (human and mouse) | Interleukin 4 encoded by Human gene IL4 and mouse gene Il4, it has been shown to promote the proliferation and differentiation of activated B cells, and synergize with Epo and G-CSF in generating granulocytes and erythroid progenitor cells colonies. A naturally occurring splice variant designated IL4-delta2 act as an antagonist. |
| IL-5 (human and mouse) | Interleukin 5. Encoded by human gene IL5 and mouse gene Il5, this protein is a specific hematopoietic factor that stimulates the growth and differentiation of eosinophils, as well as the proliferation of immature hematopoietic progenitor cells and proliferation and differentiation of immature B cells. |
| IL-6 (human and mouse) | Interleukin 6 encoded by human gene IL6, mouse gene il6. This protein stimulates specific and innate immune responses. It activates the expression of acute phase proteins in hepatocytes. IL6 and IL3 synergise to promote the proliferation of multipotent hematopoietic progenitor cells. IL6 is a B-cell differentiation factor in vivo and an activation factor for T-cells. IL6 is expressed early in murine blastocysts suggesting that it may regulate the growth and development of trophoblasts or embryonic stem cells. |
| IL-8 (human) | Interleukin 8. Encoded by the IL8 gene, this protein is found under several variants forms (from 69 aa to 77 aa). In addition its chemotactic activities IL8 is a mitogen for epidermal cells. Macrophage-derived IL8 supports angiogenesis in physiological situation such as wound repair. |
| IL-10 (human and mouse) | Encoded by the human IL10 gene (Il10 mousegene) this cytokine is a chemoattractant of CD8 cytotoxic cells and downregulator of the expression of several cytokines. |
| IL-11 (human and mouse) | Interleukin 11, encoded by human gene IL11, (mouse gene Il11) is a cytokine which in addition to promoting immune responses, stimulates several multilineages hematopoietic progenitors, inhibits the differentiation of adipocytes progenitors and induces the synthesis of acute phase proteins in hepatocytes. |
| IL-12 (human and mouse) | Interleukin 12. A heterodimeric protein encoded by the human genes IL12A and IL12B (mouse genes Il12a and Il12b), it is known to stimulate the proliferation of lymphocytes and synergizes with several factors to promote myelopoiesis of bone marrow progenitor cells. |
| IL-13 (human) | Interleukin 13. This 132 AA protein encoded by IL13 attenuates the inflammatory response. It also is known to induce differentiation of monocytes, and modulate proliferation, differentiation and Isotype switching of Bcells. |
| LIX (mouse) | Lipopolysaccharide-Induced CXC chemokine, 92 aa equivalent of human GCP2/ENA78, Renamed CLCX5, encoded by the clcx5 gene. Known as a monocytes chemoattractant produced in response to bacterial LPS. |
| MCP-1 (human and mouse) | Monocyte Chemotactic Protein 1. Renamed CCL2 and encoded by the human gene CCL2 and the mouse Ccl2 gene, this protein is chemotactic for monocytes but not neutrophils. In addition to chemotaxis. MCP-1 can induce the proliferation and activation of killer cells known as CHAK (CC-Chemokine-activated killer). |
| MCP-2 (human) | Monocyte chemotactic protein 2. Renamed CCL8, encoded by human gene CCL8, this chemotactic factor attracts monocytes, lymphocytes, basophils and eosinophils. |
| MIP-1α (mouse) | Macrophage Inflammatory Protein 1a. Encoded by Ccl3, This 92 aa protein induces synthesis of IL-1 IL-6 and TNF by fibroblasts, Synergizes with GM-CSF in promoting maturation of hematopoietic progenitor cells, while inhibiting the proliferation of hematopoietic stem cells. |
| MIP-1β (human) | Macrophage Inflammatory Protein 1beta. Encoded by CCL4, this 92 aa protein induces inflammatory response and promotes the maturation of hematopoietic progenitor cells. |
| MIP-2 (mouse) | Macrophage Inflammatory Protein 2. Encoded by the Cxcl2 gene, this 73 aa protein is chemotactic for polymorphonuclear lymphocytes. |
| RANTES | Regulated upon Activation Normal T-cell Expressed Secreted also called CCL5, this chemokine is chemotactic for T-cells, eosinophils and basophils. It also activates and proliferation of Killer cells. |
| sTNFR2 | Secreted Tumor necrosis factor receptor 2. The gene TNFRSF1B encodes the membrane bound 439 aa protein which is cleaved to a believed 235aa. The soluble form of the receptor antagonizes activity of TNFalpha by its ability to store and sequester it. |
| sTNFR1 | Secreted tumor necrosis factor receptor 1 encoded by the gene TNFR1A, the 251 aa soluble form of the TNF-α receptor 1 is thought to antagonize action of TNF-α by sequestering it. |
| TNF-α (human and mouse) | Tumor Necrosis Factor alpha is encoded by the human gene TNFA and mouse gene Tnfa TNF-a shows a wide spectrum of biological activities. In addition to its participation in inflammatory processes, TNF is a potent promoter of angiogenesis in vivo which is antagonized by IFN-gamma. It is also a growth factor for normal human diploid fibroblasts, astroglial cells and microglial cells. |

Effects of Mesenchymal Cells-Conditioned Media on Rat Hepatic Progenitor (rter6) Cell and Human Hepatoblastoma (HepG2) Cell Colony Formation rter6 are unable to generate colonies efficiently on inert substrata such as plastic or on extracellular matrix-coated plates but can produce colonies when plated on STO feeders. Hence, experiments were conducted to determine how well rter6 cells could grown in media "conditioned" by STO feeders. To generate "conditioned" media, stocks of feeders (STO cells or a human fetal lung fibroblast cell line (MRC5)) were grown in serum-supplemented medium until confluence, rinsed to remove any serum, and then switched to KM, which is serum-free. The cells were allowed to grow for another 48 hours in the serum-free medium, thus "conditioning" it with factors produced by the feeders. This conditioned media was then used in the experiments.

The colony numbers of rter6 cells co-cultured for 10 days with STO feeder cells and STO conditioned medium increased 2.39-fold compared with KM (Tables 4 and 5). The number of rter6 colonies when co-cultured for 10 days with MRC5 feeder cells and STO conditioned medium increased 1.57-fold compared with KM (Tables 4 and 5). In serum-free HDM, MRC5 cells appeared to promote more colony formation of rter6 cells compared with STO feeders. In STO conditioned medium, rter6 cells on both feeders had the similar colony formation ability.

TABLE 4

Effect of STO conditioned-medium on colony formation of rter6 cells cultured on STO or MRC5 feeder

| Rter6 seeding density (cells/cm$^2$) Average colony no. | 100 | 200 | 400 | Average fold increase of |
|---|---|---|---|---|
| HDM | 7.25 | 15.25 | 27.25 | colony no.: |
| +STO-CM | 18 | 34.5 | 66 | 2.39 |
| Fold increase | 2.49 | 2.26 | 2.42 | |
| P-value | 0.0065 | 0.0009 | 0.0003 | |

TABLE 5

Effect of STO conditioned-medium on colony formation of rter6 cells cultured on MRC5 feeder

| Rter6 seeding density (cells/cm$^2$) Average colony no. | 100 | 200 | 400 | Average fold increase of |
|---|---|---|---|---|
| HDM | 14.75 | 23.5 | 42.5 | colony no. |
| +STO-CM | 23 | 37.25 | 66.5 | 1.57 |
| Fold increase | 1.56 | 1.59 | 1.56 | |
| P-value | | | | |

Human hepatoblastoma (HepG2) cells can form colonies on uncoated tissue culture plastic. Serum-free conditioned media from four different feeder cell types were used to test the colony formation of HepG2 cells: (1) STO cells; (2) MRC5 cells; (3) immortalized adult human hepatic stellate cells (h-tert-HpSC); and (4) primary human fetal liver-derived stromal cells. Compared with HDM, the serum-free STO-conditioned medium increased colony formation of HepG2 cells, while the serum-free media conditioned by MRC5 cells, h-tert-HpSC or primary human fetal liver-derived stromal cells inhibited HepG2 cell colony formation.

Figure 12A:
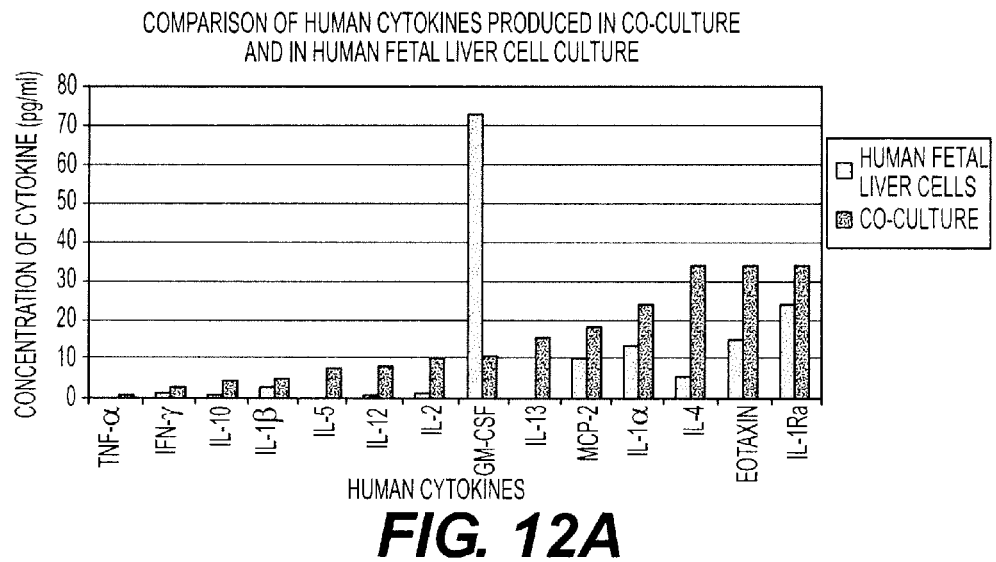
FIG. 12 provides a comparison of human cytokines produced in co-culture and in human fetal liver cell culture. Concentration (pg/ml) of human cytokines produced in human fetal liver cell single culture and in co-culture of STO feeder cells and human fetal liver cells at low (top) and high (bottom) levels.
Figure 12B:
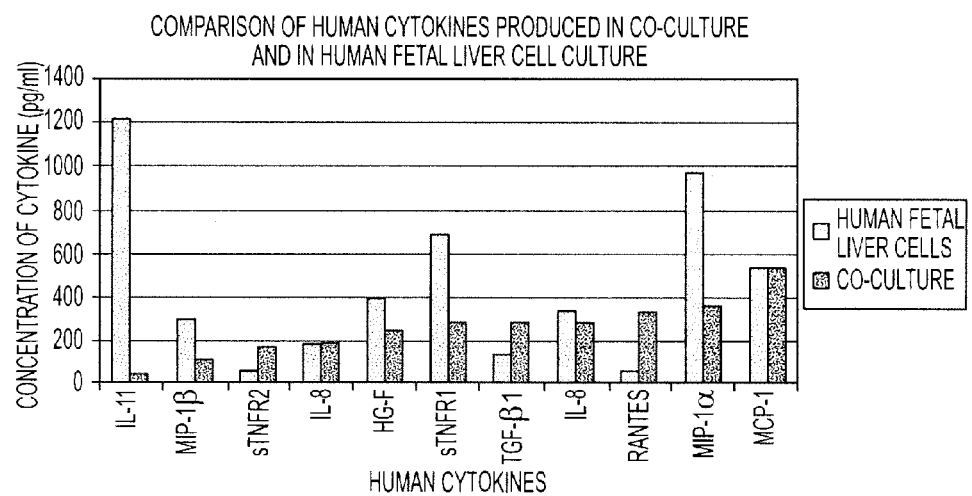

ELISA on Conditioned Media from STO Cells, Human Fetal Liver Cells, and Co-Cultures of Both The concentration of 23 human cytokines, 17 mouse cytokines and 2 non-species specific cytokines were tested on cultured media conditioned by STO feeder, human fetal liver-derived progenitor cells and co-culture of both. For human cytokines, increased concentration of soluble interleukin-1 receptorα (IL-1Rα), interleukin-1α (IL-1α), IL-2, IL-4, IL-5, IL-10, IL-12, IL-13, macrophage chemoattractant protein-2 (MCP-2), eotaxin, soluble tumor necrosis factor receptor-2 (sTNF-R2), and regulated on activation, normal T-cell expressed, and presumably secreted (RANTES) was observed in co-culture compare with human fetal liver-derived progenitor cells cultured alone (FIG. 12, Table 6). Cytokines with decreased concentration in co-culture were interleukin-11 (IL-11), granulocye macrophage-colony stimulating factor (GM-CSF), macrophage inflammatory protein-1α (MIP-1α), MIP-1β, soluble TNF receptor1 (sTNF-R1) and hepatocyte growth factor (HGF) (FIG. 12, Table 6).

TABLE 6

ELISA analyses of conditioned medium from STO cells and from human fetal liver cells

| | Concentration (pg/ml) | | | | Concentration (pg/ml) | |
|---|---|---|---|---|---|---|
| Mouse cyto-kines | STO | STO/hFLCco-culture | Human Cytokines | hFLCs | STO/hFLC co-culture Human cytokine | Human and mouse |
| TNF-α | 0 | 1.4 | TNF-α | 0 | 0.5 | 1.9 |
| IL-1β | 0 | 3 | IFN-γ | 0.8 | 2.5 | 23.4 |
| IL-12 | 0 | 11.3 | IL-10 | 1 | 4 | 62.8 |
| IL-2 | 7.7 | 12 | IL-1β | 3 | 4.8 | 7.8 |
| IFN-γ | 0 | 20.9 | IL-5 | 0 | 7.5 | 133.7 |
| GM-CSF | 5.8 | 35.3 | IL-12 | 1 | 8 | 19.3 |
| IL-11 | 0 | 46.2 | IL-2 | 0.8 | 10 | 22 |
| IL-10 | 0 | 58.8 | GM-CSF | 73 | 11 | 46.3 |
| Eotaxin | 33.96 | 68.3 | IL-13 | 0 | 16 | n/a |
| G-CSF | 2.6 | 118.7 | MCP-2 | 10 | 18 | n/a |
| IL-5 | 3.8 | 126.2 | IL-1α | 13.8 | 24.1 | n/a |
| MIP-2 | 0 | 182 | IL-4 | 5.2 | 34.3 | 317.8 |
| IL-6 | 28.2 | 192.3 | Eotaxin | 15.5 | 34.4 | 102.7 |
| MIP-1α | 86.7 | 283.17 | IL-1Rα | 24 | 34.7 | n/a |
| IL-4 | 2.3 | 283.5 | IL-11 | 1221 | 43.1 | 89.3 |
| LIX | 299 | 499 | MIP-1β | 292 | 111 | n/a |
| KC | 800 | 794 | sTNFR2 | 66 | 166 | n/a |
| MCP-1 | 2095 | 2094 | IL-8 | 172 | 177 | 971 |
| | | | HGF | 399.9 | 253.8 | n/a |
| | | | sTNFR1 | 687 | 283 | n/a |
| | | | TGF-β1 | 136.3 | n/a | 287.8 |
| | | | IL-6 | 327 | 290 | 482.3 |
| | | | RANTES | 67 | 320 | n/a |
| | | | MIP-1α | 981 | 360 | 643.17 |
| | | | MCP-1 | 539 | 531 | 2625 |

Figure 13A:
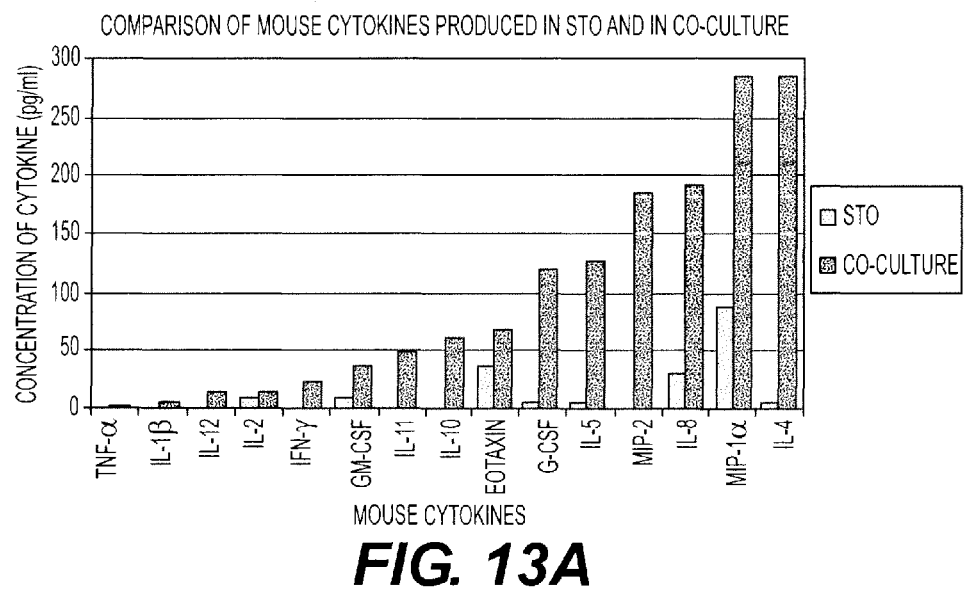
FIG. 13 provides a comparison of mouse cytokines produced in co-culture and in STO feeder cell culture. Concentration (pg/ml) of mouse cytokines produced in STO feeder cell single culture and in co-culture of STO feeder cells and human fetal liver cells at low (top) and high (bottom) levels.
Figure 13B:
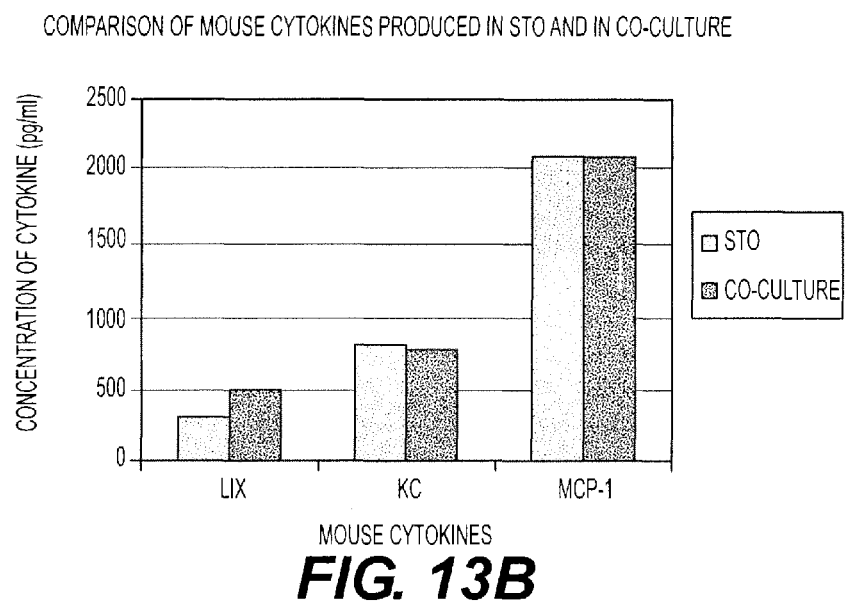

For mouse cytokines, increased concentration of interleukin-2 (IL-2), IL-4, IL-5, IL-6, IL-10, IL-11, IL-12, granulocye macrophage-colony stimulating factor (GM-CSF), eotaxin, granulocyte-colony stimulating factor (G-CSF), macrophage inflammatory protein-1α (MIP-1α), interferon-γ (IFN-β) and lipopolysaccharide-induced CXC chemokine (LIX) were observed in co-culture compared with STO cells cultured alone (FIG. 13, Table 6). There was no significant decrease of concentration of any mouse cytokines tested in co-culture.

For non-species specific cytokines, transforming growth factor-β1 (TGF-β1) was increased in co-culture (532.3 pg/ml) compared with STO cells cultured alone (10.2 pg/ml) and with human fetal liver-derived progenitor cells cultured alone (22.3 pg/ml).

Human hepatic stem cells have been found to differentiate into hepatoblasts when co-cultured with STO feeder cells. Combined concentration of human and mouse cytokines in co-culture revealed that IL-4, IL-5, IL-10, CXC chemokine (mouse keratinocyte-derived chemokines (KC) and human IL-8, eotaxin, MCP-1 and RANTES had dramatic increase (≧5-fold and >50 pg/ml) of protein concentration compared with human fetal liver cells' cultured alone (Table 6).

Effects of Soluble Cytokines on Rter6 Cells and HepG2 Cells Colony Formation

Figure 14:
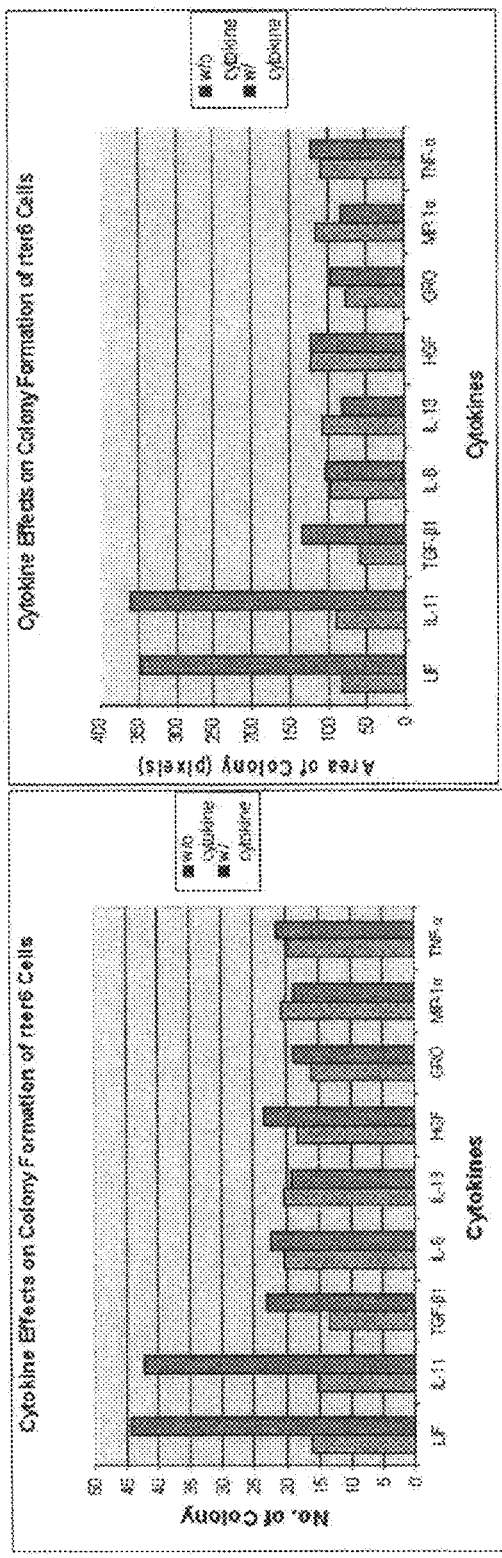
FIG. 14 shows the cytokine effects on colony formation of rter6 cells. Colony number (top) and area (in pixels; bottom) of rat hepatic progenitor (rter6) cells in hormonally defined medium (HDM) with or without cytokine are shown.

Of the cytokines uncovered, nine were added individually into serum-free, hormonally-defined medium (HDM) and tested. In addition to the media, the cells were grown on STO feeder layers and incubated for 10 days. Leukemia inhibitory factor (LIF, 0.5 ng/ml), interleukin-11 (IL-11, 10 ng/ml), and transforming growth factor-β1 (TGF-β1, 0.05 ng/ml) increased the colony number and colony area of rter6 cells compared with controls (FIG. 14). Interleukin-6 (IL-6), interleukin-13 (IL-13), hepatocyte growth factor (HGF), growth related oncogene-α (GRO-α), macrophage inflammatory protein-1α (MIP-1α) and tumor necrosis factor-α (TNF-α) had no observed effect on colony formation of rter6 cells.

Several cytokines and candidate stimulatory molecules were also added individually into HDM and STO conditioned medium to test their effects on colony formation of HepG2 cells. Hydrocortisone increased colony formation 25% in both HDM and STO conditioned medium compared with control. Insulin-like growth factor-II (IGF-II), interleukin-6 (IL-6), interleukin-11 (IL-11), interleukin-13 (IL-13), tumor necrosis factor-α (TNF-α), growth related oncogene (GRO; CXC chemokine), human growth hormones, and high density lipoproteins (HDL) had no observed effects on HepG2 cell colony formation. Transforming growth factor-β1 (TGF-β1) had inhibited HepG2 cell growth and survival. Epidermal growth factor (EGF) significantly decreased HepG2 colony formation and caused the cells to migrate away from colonies.

Taken together, the present invention enables the survival, proliferation, and/or controlled differentiation of HpSCs in the absence of feeder cells. The following Table 7 lists non-limiting examples of "feeder-free" conditions for propagating HpSCs in vitro and ex vivo. All of the examples include hyaluronans, which are ubiquitous in the stem cell niche in livers in vivo. It is thought at present that hyaluronans enhance the efficiency of propagating HpSCs. However, the examples should not be construed so as to require the presence of hyaluronans in culturing HpSCs in vitro. See, e.g., U.S. provisional patent application no. 60/893,277 filed Mar. 7, 2007, the disclosure of which is incorporated herein in its entirety by reference.

TABLE 7

| | Hyaluronans with disulfide cross-linking would be complexed with: | | | |
|---|---|---|---|---|
| Lineage Stage | Collagen(s) | Basal Adhesion Protein | Proteoglycan (or GAG chains) | Hormones and/or growth factors |
| I. Conditions for Expansion of the Cells | | | | |
| Hepatic Stem Cells and/or Hepatoblasts | Type III (and IV) collagen | Laminin | Heparan sulfate proteoglycan (or HS) from human fetal livers | Insulin, transferrin/fe, LIF, FGF4, IL6 (and/or IL11), HGF, HDL, free fatty acids on human albumin, and hepatopoietin |
| Hepatic Stem Cells and/or Hepatoblasts (mixed with angioblasts/endothelia) [grafts] | Type III (and type IV) collagen | Laminin | Heparan Sulfate proteoglycan (or HS) from human fetal livers | Insulin, transferrin/fe, LIF, FGF4, IL 6 (and/or IL11) HGF, VEGF, HDL, free fatty acids bound to human albumin, and hepatopoietin |
| II. Conditions for Differentiation of Stem/Progenitor Cells | | | | |
| Hepatic stem cells/hepatoblasts | Type IV collagen (and some type I) | Laminin/Fibronectin | Heparin Proteoglycan (or Heparin) from Adult Human Liver | Insulin, transferrin/fe T3, IGFI, HGF, hydrocortisone, HDL and free fatty acids bound to human albumin |
| III. Conditions for Growth of Adult Hepatocytes | | | | |
| Hepatocytes (diploid cells must be used for complete cell division) | Type IV collagen | Laminin | Heparan sulfate proteoglycan (or HS) from fetal human livers | Insulin, EGF, T3, IGFI, HGF, HDL, free fatty acids bound to human albumin, hepatopoietin |
| IV. Conditions for Maximal Differentiation of Adult Hepatocytes | | | | |
| Hepatocytes (both diploid and polyploid cells) | Type I collagen (with small amounts of type III) | Fibronectin | Heparin Proteoglycan (or Heparin) from Adult human livers | Insulin, EGF, T3, IGFI, HGF, Hydrocortisone, HDL, Free Fatty Acids bound to human albumin, and glucagon |

In this way, transplanted cells obviate whole organ replacement all together. Furthermore, in vitro devices such as bioreactors may be seeded with hepatic progenitors enveloped in an appropriate extracellular matrix and soluble signaling environment so they populate device subcompartments with viable tissue structures. In this way, bioartificial devices can be utilized for pharmacology studies, vaccine developments, and as a bridge between organ failure and organ transplantation. Indeed, the results obtained from these investigations suggest that utilizing these cells may be an avenue to improve cell sourcing limitations that currently inhibit both cell therapy and bioreactor device medical treatments options.

While the invention has been described in connection with specific embodiments thereof, it will be understood that it is capable of further modifications and this application is intended to cover any variations, uses, or alterations of the invention following. In general, the principles of the invention and including such departures from the present disclosure as come within known or customary practice within the art to which the invention pertains and as may be applied to the essential features hereinbefore set forth and as follows in the scope of the appended claims.

We claim:

1. A method of propagating human hepatic stem cells in vitro without inducing their differentiation comprising: culturing a population of isolated hepatic stem cells in serum-free culture media and on a layer of human umbilical vein endothelial cells (HUVEC) feeder cells,
    in which the layer is essentially free of mature collagens, and in which the culturing propagates the hepatic stem cells without inducing their differentiation.

2. The method of claim 1, in which the layer further comprises a matrix component selected from the group consisting of hyaluronans, unsulfated or poorly sulfated glycosaminoglycans (GAGs), unsulfated or poorly sulfated proteoglycans, embryonic collagens and embryonic basal adhesion molecules, and combinations thereof.

3. The method of claim 2, in which the embryonic collagens are of type III, type IV, or both.

4. The method of claim 2, in which the layer is essentially free of collagen type I.

5. The method of claim 2, in which the basal adhesion molecules comprise isoforms of laminin found predominantly in fetal tissues.

6. The method of claim 2, in which the GAGs are forms of chondroitin sulfates.

7. The method of claim 2, in which the proteoglycans are forms of chondroitin sulfate proteoglycans (CS-PGs).

8. The method of claim 2, in which the hepatic stem cells are obtained from fetal, neonatal, pediatric or adult liver.

9. The method of claim 5, in which the laminin is at a concentration between about 0.1 to about 2 μg/cm$^2$.

10. The method of claim 9, in which the laminin is at a concentration of about 1 μg/cm$^2$.

11. The method of claim 3, in which the type III or IV collagens are individually at a concentration between about 0.1 to about 15 μg/cm$^2$.

12. The method of claim 2, in which the layer comprises hyaluronans.

* * * * *